United States Patent
Aidun

(10) Patent No.: US 10,004,189 B2
(45) Date of Patent: *Jun. 26, 2018

(54) SEPARATOR DEVICE, DEPOSITION DEVICE AND SYSTEM FOR HANDLING OF SOMATIC PLANT EMBRYOS

(71) Applicant: Georgia Tech Research Corporation, Atlanta, GA (US)

(72) Inventor: Cyrus K. Aidun, Marietta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 473 days.

This patent is subject to a terminal disclaimer.

(21) Appl. No.: 14/693,250

(22) Filed: Apr. 22, 2015

(65) Prior Publication Data

US 2015/0225693 A1 Aug. 13, 2015

Related U.S. Application Data

(63) Continuation-in-part of application No. 13/500,886, filed as application No. PCT/IB2010/054557 on Oct. 8, 2010, now Pat. No. 9,040,301.

(Continued)

(30) Foreign Application Priority Data

Oct. 9, 2009 (SE) ...................... 0950742

(51) Int. Cl.
*A01H 4/00* (2006.01)

(52) U.S. Cl.
CPC .................... *A01H 4/001* (2013.01)

(58) Field of Classification Search
CPC . A01H 4/001; A01H 4/00; C12N 5/00; C12N 5/04; C12M 45/02; C12M 23/58; C12M 33/12; C12M 33/10; C12M 47/04; C12M 1/00; B04C 5/04; B04B 2005/0471; Y10S 435/813; B07B 4/08

(Continued)

(56) References Cited

U.S. PATENT DOCUMENTS 4,146,468 A 3/1979 Wilson
4,959,158 A 9/1990 Meikrantz (Continued)

FOREIGN PATENT DOCUMENTS

CN 101035426 A 9/2007
EP 1498025 A2 1/2005

(Continued)

OTHER PUBLICATIONS

Office Action received for Australian Patent Application No. 2014262226, dated Feb. 17, 2016, 5 pages.

(Continued)

*Primary Examiner* — Kent L Bell
(74) *Attorney, Agent, or Firm* — Morrison & Foerster LLP

(57) ABSTRACT

Methods and devices for separating fluid-suspended plant propagules and non-plant propagules based on differences in their fluid drag properties are disclosed. Deposition method and device for depositing plant propagules into a receiver comprising growth substrate by means of a fluid jet is disclosed. An automated system for processing plant propagules from a bioreactor to the growth substrate is also disclosed.

**28

Related U.S. Application Data

(60) Provisional application No. 61/250,015, filed on Oct. 9, 2009.

(58) Field of Classification Search
USPC ... 435/420, 430, 285.1, 286.1, 286.5, 286.7, 435/289.1, 813; 209/725, 551; 210/512.1, 788
See application file for complete search history.

(56) References Cited

U.S. PATENT DOCUMENTS

| | | | |
|---|---|---|---|
| 5,284,765 A | 2/1994 | Bryan et al. | |
| 5,563,061 A | 10/1996 | Gupta | |
| 5,591,340 A | 1/1997 | Meikrantz et al. | |
| 5,821,116 A | 10/1998 | Herman | |
| 6,193,647 B1 | 2/2001 | Beebe et al. | |
| 6,684,564 B1 | 2/2004 | Hirahara | |
| 7,568,309 B2 | 8/2009 | Hirahara | |
| 8,394,633 B2 | 3/2013 | Aidun | |
| 8,975,077 B2 | 3/2015 | Aidun | |
| 9,040,301 B2 * | 5/2015 | Aidun | C12N 5/00 435/420 |
| 2005/0114918 A1 | 5/2005 | Hirahara et al. | |
| 2005/0246802 A1 | 11/2005 | Attree et al. | |
| 2008/0108137 A1 | 5/2008 | Rigaut | |
| 2012/0202289 A1 | 8/2012 | Aidun | |
| 2013/0153691 A1 | 6/2013 | Aidun | |

FOREIGN PATENT DOCUMENTS

| | | |
|---|---|---|
| WO | 1996/025484 A1 | 8/1996 |
| WO | 2009/029852 A2 | 3/2009 |
| WO | 2009/126757 A2 | 10/2009 |
| WO | 2009/126758 A1 | 10/2009 |
| WO | 2011042888 A2 | 4/2011 |

OTHER PUBLICATIONS

Office Action received for European Patent Application No. 09730557.7, dated Mar. 25, 2011, 3 pages.
European Search Report received for European Patent Application No. 10821666.4 dated Sep. 13, 2013, 8 pages.
Extended European Search Report received for European Patent Application No. 10821666.4 dated Jun. 26, 2013, 6 pages.
Final Office Action received for U.S. Appl. No. 12/937,240, dated Aug. 27, 2012, 7 pages.
Non Final Office Action received for U.S. Appl. No. 12/937,240, dated Feb. 23, 2012, 6 pages.
Non Final Office Action received for U.S. Appl. No. 12/937,240, dated Jan. 9, 2012, 9 pages.
Notice of Allowance received for U.S. Appl. No. 12/937,240, dated Nov. 19, 2012, 7 pages.
Restriction Requirement received for U.S. Appl. No. 12/937,240, dated Nov. 11, 2011, 7 pages.
Non-Final Office Action received for U.S. Appl. No. 13/500,886, dated May 22, 2014, 6 pages.
Notice of Allowance received for U.S. Appl. No. 13/500,886, dated Jan. 22, 2015, 20 pages.
Non-Final Office Action received for U.S. Appl. No. 13/500,904, dated Jun. 5, 2014, 8 pages.
Restriction Requirement received for for U.S. Appl. No. 13/500,904 dated Jan. 29, 2014, 5 pages.
Restriction Requirement received for for U.S. Appl. No. 13/500,904 dated Oct. 21, 2013, 5 pages.
Final Office Action Received for U.S. Appl. No. 13/761,125, dated Jul. 1, 2014, 5 pages.
Non Final Office Action received for U.S. Appl. No. 13/761,125, dated Jun. 27, 2013, 7 pages.

Non-Final Office Action received for U.S. Appl. No. 13/761,125, dated Jan. 30, 2014, 7 pages.
Restriction/Election Requirement received for U.S. Appl. No. 13/761,125, dated May 3, 2013, 5 pages.
Office Action received for Chinese Patent Application No. 200980112745.4, dated Dec. 29, 2011, 10 pages.
Office Action received for Chinese Patent Application No. 201080045536.5, dated Mar. 15, 2013, 22 pages.
Office Action received for Chinese Patent Application No. 201080045552.4, dated Jul. 15, 2013, 15 pages.
Examination Report received for New Zealand Patent Application No. 599717, dated Feb. 28, 2014, 2 pages.
Office Action received for New Zealand Patent Application No. 599717, dated Dec. 4, 2012, 1 Page.
International Preliminary Report on Patentability received for PCT Patent Application No. PCT/IB2010/054557, dated Apr. 19, 2012, 8 pages.
International Search Report and Written Opinion received for PCT Patent Application No. PCT/IB2010/054557, dated Apr. 22, 2011, 10 pages.
International Preliminary Report on Patentability received for PCT Patent Application No. PCT/SE2010/051083, dated Apr. 19, 2012, 10 pages.
International Search Report and Written Opinion received for PCT Patent Application No. PCT/SE2010/051083, dated Nov. 9, 2010, 12 pages.
International Preliminary Report on Patentability received for PCT Patent Application No. PCT/US2009/039981, completed on Mar. 22, 2010, 4 pages.
International Search Report received for PCT Patent Application No. PCT/US2009/039981, dated Sep. 3, 2009, 3 pages.
Written Opinion of the International Search Authority received for PCT Patent Application No. PCT/US2009/039981, dated Sep. 30, 2009, 4 pages.
Belmonte et al., "Alterations of the Glutathione Redox State Improve Apical Meristem Structure and Somatic Embryo Quality in White Spruce (*Picea glauca*)", Journal of Experimental Botany, vol. 56, No. 419, Sep. 2005, pp. 2355-2364.
Greenspan et al., "On the Centrifugal Separation of a Bulk Mixture", International Journal of Multiphase Flow, vol. 11, No. 6, 1985, pp. 825-835.
Harrell et al., "Machine Vision Based Analysis and Harvest of Somatic Embryos", Computers and Electronics in Agriculture, vol. 9, No. 1, 1993, pp. 13-23.
Prasheh et al., "Variation of Fiber Orientation in Turbulent Flow Inside a Planar Contraction with Different Shapes", International Journal of Multiphase Flow, vol. 32, No. 12, Dec. 2006, pp. 1354-1369.
Rodriguez et al., "Mechanical Purification of Torpedo Stage Somatic Embryos of Daucus Carota L", Plant Cell, Tissue and Organ Culture, vol. 23, No. 1, 1990, pp. 9-14.
Von Arnold et al., "Spruce Embryogenesis", Methods Molecular Biology, vol. 427, 2008, pp. 31-47.
Notice of Allowance received for U.S. Appl. No. 13/500,904, dated Sep. 22, 2014, 7 pages.
Notice of Allowance received for U.S. Appl. No. 13/500,904, dated Nov. 10, 2014, 5 pages.
Notice of Allowance received for U.S. Appl. No. 13/500,904, dated Sep. 30, 2014, 2 pages.
Notice of Allowance received for U.S. Appl. No. 13/761,125, dated Nov. 3, 2014, 7 pages.
Invitation to Pay Additional Fees received for PCT Patent Application No. PCT/IB2010/054557, dated Jan. 25, 2011, 2 pages.
Non-Final Office Action received for U.S. Appl. No. 14/642,690, dated Jul. 6, 2016, 6 pages.
Notice of Allowance received for U.S. Appl. No. 14/642,690, dated Dec. 14, 2016, 5 pages.
Office Action received for Canadian Patent Application No. 2,775,907, dated Nov. 7, 2016, 5 pages.

* cited by examiner

A

B a b f

SEPARATOR DEVICE, DEPOSITION DEVICE AND SYSTEM FOR HANDLING OF SOMATIC PLANT EMBRYOS

CROSS REFERENCE TO RELATED APPLICATIONS

This application is a continuation-in-part of U.S. application Ser. No. 13/500,886, filed Apr. 6, 2012, which is a U.S. National Phase patent application of PCT/IB2010/054557, filed Oct. 8, 2010, which claims priority to the Swedish Patent Application No. 0950742-7, filed Oct. 9, 2009, and the U.S. Provisional Patent Application No. 61/250,015, filed Oct. 9, 2009, each of which is hereby incorporated by reference in the present disclosure in its entirety.

BACKGROUND TO THE INVENTION

General Introduction to Problem Area

Somatic embryogenesis in plants is a process in which somatic embryos are formed from an initial explant being a cell in a plant tissue. The somatic embryos formed are genetically identical copies of the plant providing the initial explant. The process of somatic embryogenesis thereby offers a tool to obtain large numbers of genotypically identical plants for multiplication of selected genotypes of commercial interest, for conservation of endangered species or for generating genetically uniform plant material for research purposes.

Physiological Background to the Procedures Related to the Problem

To produce plants from somatic embryos of conifers, a multi-step procedure is applied to meet the physiological needs of the different stages of development as described below and shown in FIG. 1. Initiation of somatic embryogenesis starts with induction of somatic embryos from an initial explant, typically an immature zygotic embryo, on a solidified culture medium containing plant growth regulator. Somatic embryos continue to form, typically on the same composition culture medium, and a proliferating embryogenic culture form. At the proliferating stage, several of the key features generally regarded as beneficial for the process of somatic embryogenesis process, take place: (i) the mass propagation of genotypically identical propagules through unlimited multiplication of immature embryogenic tissue; (ii) cryogenic storage of proliferating embryos substantiates an virtually eternal store of clones, i.e. a clone bank is established, (iii) transgenic modification of the immature somatic embryo allow for large scale propagation of genetically improved propagules. At the next step in the procedure, the proliferating somatic embryo is subjected to a growth medium that triggers embryo development to progress into the maturation stage. Conversion from proliferation to maturation only occurs in a fraction of the proliferating embryos in the culture. Low conversion rates are encountered more frequently in genotypes from recalcitrant conifer species, but are common in all conifer species as well as other plant species. The manual labour needed to collect embryos increase with the decrease in conversion rate, and thereby the cost and risk of contamination and other inaccuracies. Low conversion rate from proliferation to maturation is a major bottleneck for commercial large scale applications of somatic embryogenesis procedures. For germination, mature somatic embryos are subjected to different culture regimes to induce root- and shoot formation, in a number of different steps; desiccation, sucrose treatment, red light induction, and blue light stimulation. Thereafter, germinated embryos deemed appropriately developed are transferred to a compost material and gradually transferred to an environment ex vitro during which the sucrose content is reduced. The different treatments during germination into a plant requires repeated manual handling of individual germinants and plants adding a considerable cost to the overall procedure.

Production of Plants from Somatic Embryos

The prior art procedure for producing plants from somatic embryos requires manual handling at several steps making the procedure time consuming, expensive and inaccurate.

For conifer species, standard procedures used involve several steps when manual handling is required. The general procedure is outlined in FIG. 1 (see e.g. von Arnold S, Clapham D. Spruce embryogenesis. 2008. *Methods Mol Biol*. 2008; 427:31-47; Belmonte M F, Donald G, Reid D M, Yeung E C and Stasolla C. 2005. Alterations of the glutathione redox state improve apical meristem structure and somatic embryo quality in white spruce (*Picea glauca*). *J Exp Bot*, Vol. 56, No. 419, pp. 2355-2364).

There are four steps that rely on manual handling to obtain a small plant from the mature somatic embryo as seen in FIG. 1. The first manual interaction is when [1] the mature embryo is isolated from immature embryos (120), and placed horizontally in a plastic container under sterile conditions; the second [2] occur after 3-7 days of resting (130), then mature embryo is transferred to a gelled culture medium for initiation of germination processes. The germinated somatic embryo will under appropriate culture medium composition and light conditions initiate roots (140). The third manual transfer [3] is when the germinant having a small root formed is transferred to an upright position with the root partially immersed in liquid germination media (150). The fourth [4] and final transfer is when the germinated embryos has a tap root and small lateral roots, then it is transferred into a solid substrate in a pot for further plant formation (160).

TABLE 1

List of designations pertaining to FIG. 1.

| Item | Designation |
| --- | --- |
| 100 | Mature embryo |
| 101 | Crown of a mature embryo |
| 102 | Foot of a mature embryo |
| 103 | Width of crown of a mature embryo |
| 104 | Length of a mature embryo |
| 120 | Maturation phase |
| 130 | Resting phase |
| 140 | Germination phase |
| 150 | In vitro plant formation phase |
| 160 | Ex vitro plant formation phase |

In the hitherto available method for producing plants from somatic embryos the embryos are picked out manually from the immature embryogenic tissue. This is time-consuming and ineffective. Prior art U.S. Ser. No. 06/684,564 and U.S. Pat. No. 7,568,309 teach automation of the manual transfers by replacing human eye, human arm and tweezers with vision systems, conveyer belts and automated robotic arms with suction tips to pick up the embryos from porous conveyer belts to deposit in a destination much like a human does the same. However, this approach, analogous to automating the wing motion of a bird by robotic wings for flight, is too complex and impractical for several reasons, as elaborated below. It would therefore be desirable to provide a simple and practical way to make the separation and deposition of the embryos faster and more efficient. The mature somatic embryos produced are initially glued together with immature embryogenic tissue in clusters. This makes the process more complex, as embryos have to first be separated from the immature embryogenic tissue in the cluster by breaking up the cluster. Prior art does not teach how to breakup the embryogenic clusters in an automated manner.

Breaking Up the Clusters by a Disperser

In the patent application PCT/US09/39981 a method of rapidly breaking up the clusters is disclosed based on suspending the said clusters in liquid medium, such as water, and forcing the clusters into at least one dispersion sequence where the clusters of embryogenic mass are exposed to flow-dynamic forces causing the breakup of the clusters and dispersion of individual embryos.

Segregation of Embryos by a Separator

When embryogenic mass is dispersed in liquid according to the above-presented method, a mixture of immature and mature embryos and immature embryogenic tissue are suspended in the liquid medium. In many applications, it is highly desirable to segregate and collect the embryos from the dispersed embryogenic mass prior to processing further downstream. For example, if the intention is to image and analyze the shape and condition of the embryos, such as in Harrell et al., 1993 (Computers and Electronic in Agriculture, 9), it is highly desirable to only have embryos suspended in liquid without any of the immature embryogenic tissue in order to avoid obscuring the image. The tasks of image recognition and analysis become more difficult and tedious if the image contains more objects than just the embryo. Furthermore, the task of image processing will be more time consuming with adverse impact on the processing and the conversion rates. Thus there is a need for methods and means for an effective separator to segregate and selectively remove and guide only the embryos from the dispersed embryogenic mass into a separate flow stream in a rapid and efficient manner. Having only individual embryos in a flow stream would facilitate further processing of the embryos which may include digital imaging of the individual embryos, image analysis and characterization of the embryos including identification and control of embryo orientation prior to deposition into an appropriate substrate for germination and plant production.

It is an object of the invention to provide an automated means for gently segregating and separating dispersed somatic embryos from the immature embryogenic tissue and guiding the collected embryos into a separate stream of liquid in a rapid and efficient manner.

Embryo Deposition Means

The prior art methods to make plants from somatic embryos require intensive manual handling, and are therefore expensive for plant production. Attempts to automate the steps used in the manual operation have failed due to the complex devices developed to automate the manual transfer and delivery of embryos by means of moving parts such as conveyer belts and elaborate robotic arms. For example, the prior art documents U.S. Pat. No. 7,568,309 and U.S. Pat. No. 6,684,564 teach means of transferring the embryos into an artificial seed by means of a porous conveyer belt and moving robotic arms equipped with suction tips to pick up the embryo from the conveyer belt and to deposit the embryo by means of a movable robotic arm attached to a rail into an artificial seed. Such processes require many moving parts such as pulleys and motors to drive the conveyer belt, suction device(s) to vacuum excess liquid from the embryo, and elaborate robotic arm assembly movably attached to a rail with precision control to locate and pick the embryo from the conveyer belt. The embryo being a small and delicate object, the robotic arm must have sensitive and precise means of picking and carrying the embryos without damaging it. As explained in U.S. Pat. No. 6,684,564, the conveyer belt must stop moving when an embryo is detected in order for the embryo to be imaged and picked up by mechanical means of a robotic arm. A conveyer belt that has to move and stop each time an embryo is detected creates an inherently inefficient process. In general, the prior art teaches an approach requiring many moving parts including the conveyer belts and the robotic arm assemblies making the current state of the art to be impractical.

Thus, one object of the invention is to provide an advantageous method and device for delivering an embryo to a desired embryo receiver, not requiring any pulleys, conveyer belts, robotic arms or such devices with moving parts.

System

It is another object of the invention to provide a system for processing plant somatic embryos performing the separation process and at least one additional process step of the entire process from a bioreactor to a planted propagule, providing cost-effective means for handling and large-scale production of plants from somatic embryogenesis.

DEFINITIONS

The term "plant propagule" refers to a plant, a part of a plant or a vegetative part of a plant, such as a bud or a plantlet that becomes detached from the rest of the plant and grows into a new plant. A plant propagule may also refer to any plant material that is used for the purpose of propagating a plant to the next stage in their life cycle. Further, a plant propagule may be a woody, semi-hardwood, or softwood cutting, leaf section, or any number of other plant parts. In micro-propagation of a plant propagule, any part of the plant may be used, though it is usually a highly meristematic part such as root and stem ends or buds. A mature somatic embryo is also referred to as a plant propagule. A plant propagule can be grown outdoors, indoors or cultured in vitro. The term "plant propagule" includes plants germinated from seeds, somatic embryos and in vitro grown shoots from calluses or cuttings.

In the description of this invention somatic embryos or embryos can be interchangeable with plant propagules or propagules.

The term "non-plant propagule tissue" is in this context referred to as the part of a plant, the part of a plant, the plant tissue or the vegetative part of a plant, such as a bud, that is the rest when a "plant propagule" is removed. In the case a plant propagule is coming from a woody cutting, semi-hardwood cutting, or softwood cutting, leaf section, or any other plant parts, then the non-propagable, non-living, non-reproducible part is referred to as the "non-plant propagules"

In the description of this invention immature embryogenic tissue and embryogenic tissue can be interchangeable with "non-plant propagules" or "non-plant propagule tissue".

For purposes herein, the terms somatic embryo, embryo and plant somatic embryo are used interchangeably. The terms refer to plant embryos derived from somatic tissue of a plant, whether mature or immature.

The term embryogenic mass refers collectively to the plant material consisting of immature embryogenic tissue, or mature embryos and immature embryogenic tissue, present in the liquid or solid culture of somatic embryos.

The term immature embryogenic tissue refers to all material other than embryos that are in the embryogenic mass. The term tissue is being used here in an unconventional manner consisting of largely undifferentiated cells and should not to be confused with the normal reference to plant tissue with specialized cells.

The terms embryogenic clusters, embryo clusters or clusters, are used interchangeably. The term refers to assemblies of plant embryogenic mass held together as a continuous solid material of finite size on solid medium or in liquid medium.

Norway spruce is a spruce species with the Latin name *Picea abies* native to Europe.

The orthogonal directions in polar coordinates are given by axial (z), radial (r) and angular (or azimuthal) (θ) directions. These directions correspond to the central axis of a cylinder which is normal to the circular cross-sectional of the cylinder. The radial and angular directions point along the radius and normal to the radius on the cross-sectional surface respectively.

Axisymmetric flow refers to flow inside a tube where the cross-sectional surface of the tube is always circular, and therefore, there is symmetry with respect to the axis of the tube. In other words, nothing changes along the angular (or azimuthal) direction.

Pressure gradient refers to the rate of variation of pressure with respect to a given axial direction.

Axial, radial, angular pressure gradient refers to variations in pressure (p) in the axial, radial, and angular directions shown respectively in mathematical terms as partial derivatives $$\frac{\partial p}{\partial z}, \frac{\partial p}{\partial r}, \frac{\partial p}{\partial \theta}.$$

The term Vortex (plural Vortices), as used here, is a term referred to a flow that possesses vorticity with a spinning or swirling motion around a central axis. Vortex flow can be categorized as free (irrotational) vortex or forced (rotational) vortex.

As used here, the term Vorticity in mathematical terms, is the curl of the velocity vector field; therefore, it is a vector quantity with magnitude and direction. In other terms, the value of vorticity at a point in the flow is related to rate of rotation of the fluid particles at a point in the flow field.

The term Free vortex, as used here, refers to a vortex flow where the fluid particles retain their orientation while the flow rotates around an axis (i.e., vorticity is zero) everywhere in the flow except near the central axis (where in mathematical terms, a singularity exists). Placing a hypothetical arrow moving with the fluid particles, the arrow continues to point in the same direction while it rotates around the axis with the flow. An ideal irrotational sink vortex could be an example of a free vortex.

The term sink vortex as used here refers to the actual flow field produced in the vicinity of a drainage region, said drainage could be by any means including natural drainage directed downward by gravity or drainage in any direction induced by pressure differential or other means.

The term Forced vortex, as used here, refers to a vortex flow where the fluid moves in a solid-body rotation; meaning that there is no shear in the flow and therefore the vorticity is constant everywhere and equal to 2ζ, where ζ is the rate of rotation. A hypothetical arrow pointing to the axis of rotation and attached to the fluid particles in a Forced vortex continues to point to the axis of rotation while rotating around the axis.

Cotyledon a part of a plant embryo (100) that becomes the embryonic first leaves of a seedling. The cotyledon is located at one end of a plant embryo opposite to the end where roots will eventually form (foot (102)). When there are several cotyledons, the may form a structure referred to as a crown (101).

Diameter of the crown refers to the diameter of a crown structure at its widest (103).

Length of a plant embryo refers to the linear distance from the tip of the root end to the tip of the cotyledon end measured along the longitudinal axis of the embryo (104).

The terms tube, channel and flow channel are used interchangeably. The terms are used without specific reference to any particular geometric shape of the cross-section, unless specifically stated otherwise.

The terms fluid dynamics and hydrodynamics are used interchangeably and refer to the same physical principles of flow of fluids.

Strain is the geometrical measure of deformation representing the relative displacement between points in the material body; it is represented as the ratio or percentage of deformation in relation to the original dimension.

Normal strain defines the ratio or percentage amount of stretch or compression along material line elements (ratio of the deformation to the original length in the direction of the deformation).

Shear strain defines the ratio or percentage amount of deformation relative to the original dimension associated with the sliding of material plane layers over each other.

Extensional strain is a normal strain where the element stretches.

Axially extensional strain is an element that stretches along the axial direction.

Radially extensional strain is an element that stretches along the radial direction.

Compressional strain is a normal strain where the element contracts.

Axially compressional strain refers to deformation of an element that contracts along the axial direction.

Radially compressional strain refers to deformation of an element that contracts along the radial direction.

Rate of Stain is the change in strain with respect to time

Hydraulic diameter, $D_h$, is a term used to characterize flow in noncircular tubes and channels. By definition, it is given by $D_h = 4 A/S$ where A is the cross-sectional area of the noncircular tube or channel and S is the wetted perimeter of the cross-section.

Mean velocity in a channel is defined as the volumetric flow rate divided by the cross-sectional area of the channel.

Contraction ratio is defined as the ratio of the mean velocity at the outlet to the mean velocity at the inlet in a channel.

Mean stress is the stress that is averaged over a surface.

Mean rate of strain is the rate of strain averaged over a surface.

Dynamic viscosity of a fluid is the ratio of shear stress to rate of shear strain, a constant for a Newtonian fluid. Water, glycerin, silicone oil are examples of Newtonian fluids.

Rate of strain profile is a profile showing the variation of the rate of strain.

Unit of length in millimetre is abbreviated as "mm".

Unit of rate of strain as reciprocal second is abbreviated as "1/s".

In general, a flow with higher average rate of strain will impose higher average stress on a particle (or embryo) or on a cluster of particles (or cluster of embryos) suspended in the fluid.

The terms boundary layer, viscous boundary layer, and thin boundary layer are used interchangeably to mean the boundary layer formed by a forced rotating flow inside the circular container with or without the presence of a sink boundary layer.

TABLE 2

Figure 1:
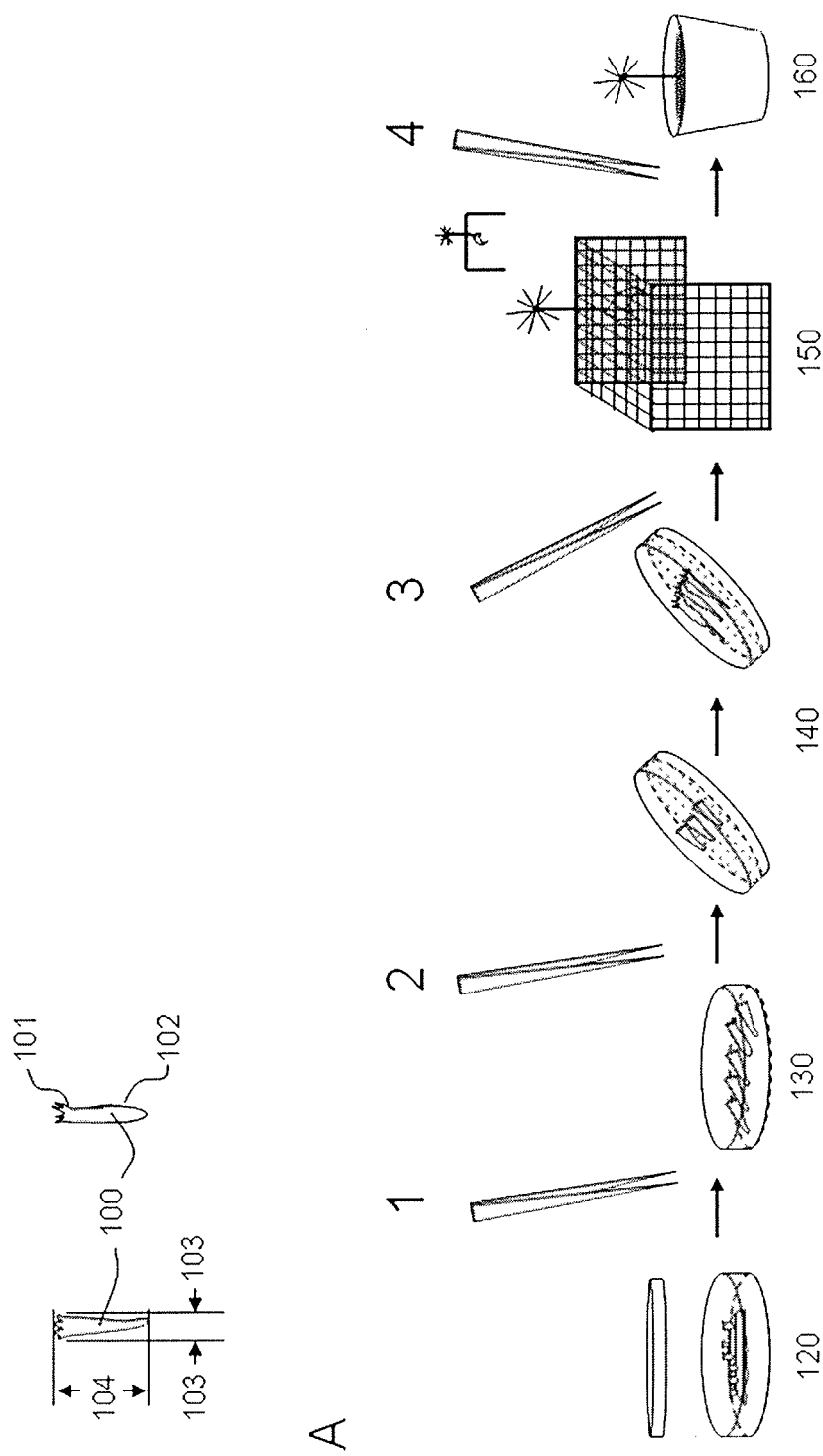
FIG. 1 Illustrates a general process of producing somatic plant embryos.
Figure 2:
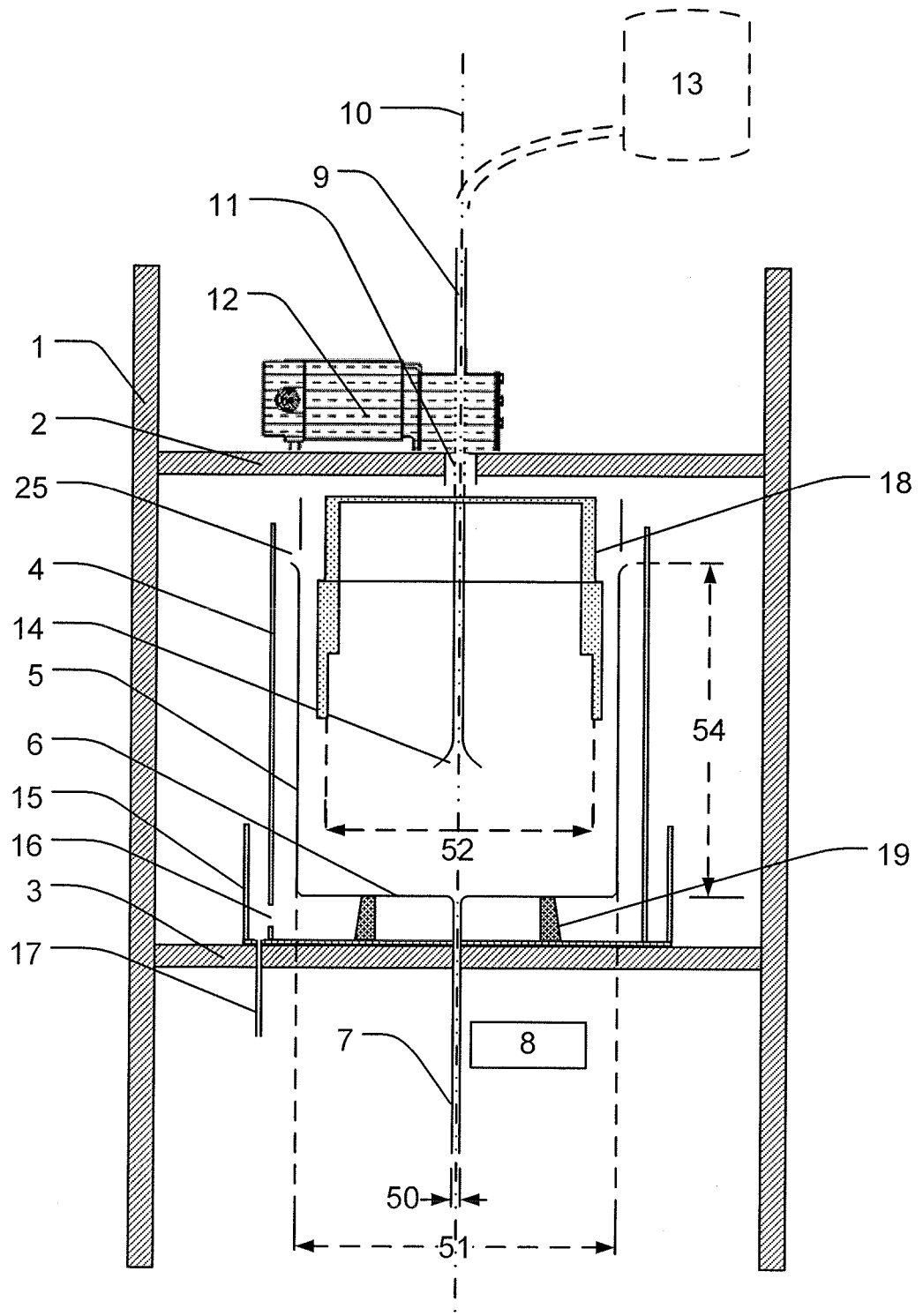
FIG. 2. illustrates the construction of certain details of a certain embodiment of a separator device of the invention.
Figure 3:
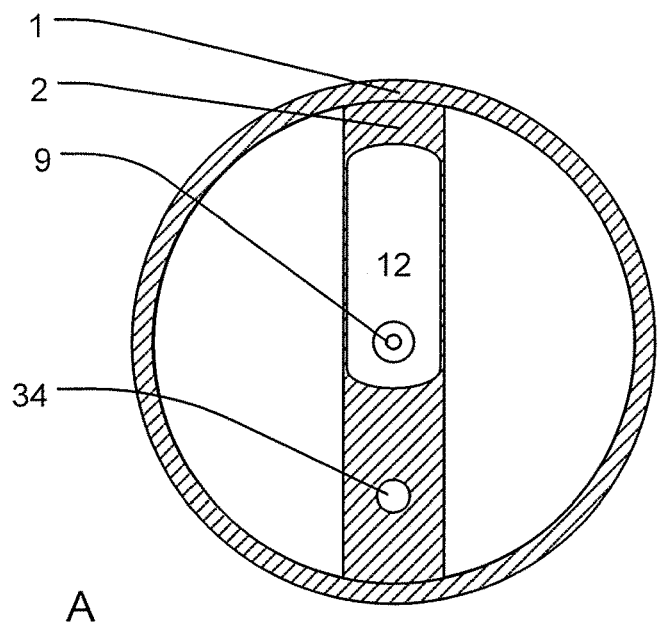
FIG. 3. Top and bottom view of a certain embodiments of a separator device of the invention FIG. 4. Shows the liquid level in the inner separator container (5), before operation (A) and during operation (B).
Figure 3:
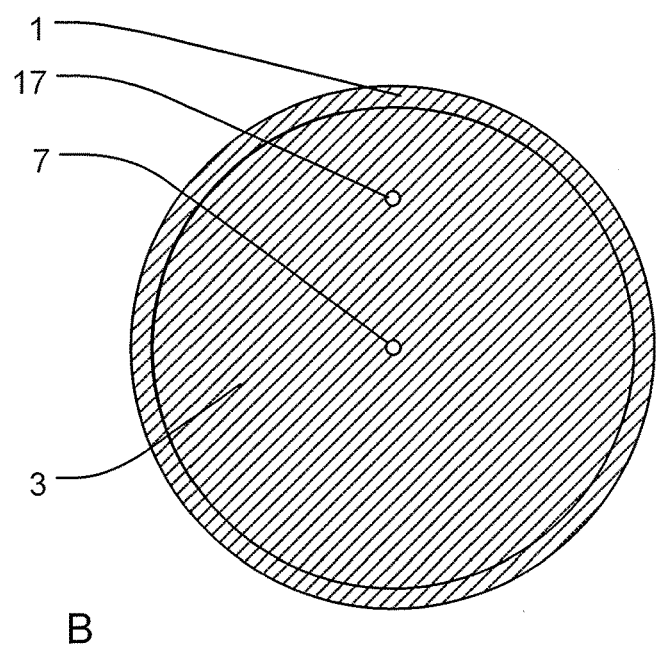
Figure 4:
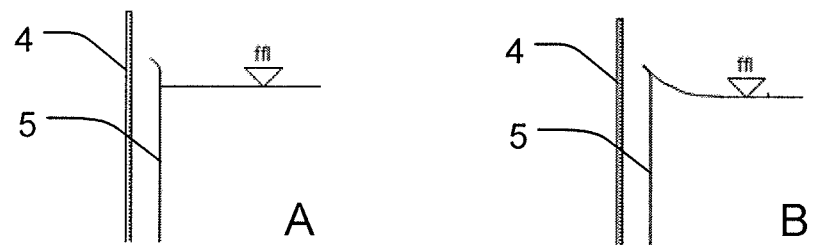
Figure 5:
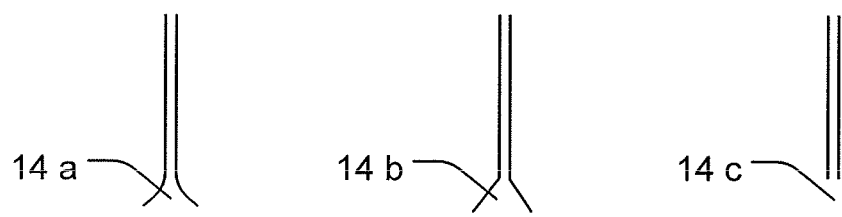
FIG. 5. Illustrates different alternative embodiments of the outlets of the feed tube (14a, 14b, 14c).
Figure 6:
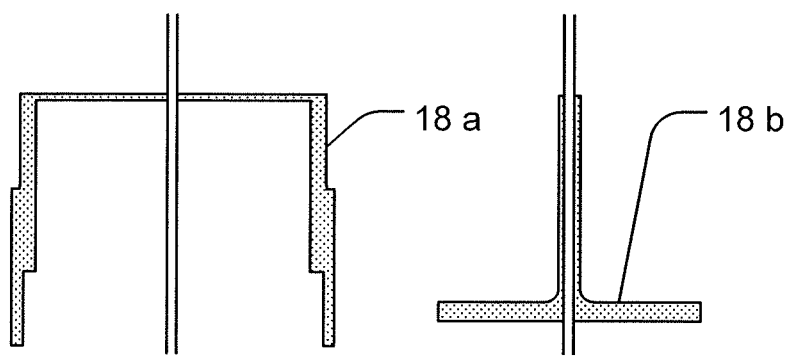
FIG. 6. Illustrates different alternative embodiments for the rotating means (18a, 18b).

| | List of designations pertaining to the Figures. |
|---|---|
| 1 | House Frame |
| 2 | Top support structure |
| 3 | Bottom support structure |
| 4 | Outer container |
| 5 | Separator container |
| 6 | Bottom wall of separator container |
| 7 | Conduit of separator container |
| 8 | Sensor |
| 9 | Feed conduit |
| 10 | Axial centre of separator container (5) |
| 11 | Hollow shaft |
| 12 | Hollow-shaft motor |
| 13 | Upstream container |
| 14 | Outlet of feed conduit (9) |
| 15 | Liquid barrier of outer container |
| 16 | Opening in the outer container |
| 17 | Outer container draining tube |
| 18 | Rotation means |
| 19 | Base block |
| 20 | Boundary layer |
| 21 | Fluid level in the separator container at start |
| 22 | Fluid level in the separator container during operation |

TABLE 2-continued

| | List of designations pertaining to the Figures. |
|---|---|
| 25 | Secondary outlet |
| 30 | Third outlet from container (5) |
| 31 | Separator container (5) draining tube |
| 32 | Extraction tube |
| 33 | Bottom end of Extraction tube |
| 34 | Hole in top support structure |
| 35 | Linear actuator |
| 36 | Valve, such as a pinch, gate, drop-through rotary or needle valve, or a set of such valves (optional) |
| 37 | Draining valve (optional) |
| 38 | Controlling unit (optional) |
| 50 | Inner diameter of a circular embodiment of an conduit (7) |
| 51 | Inner diameter of a circular embodiment of a separator container (5) |
| 52 | Inner diameter of an embodiment of rotating means 18 a |
| 53 | Diameter of an embodiment of rotating means 18 b |
| 54 | Height of separator container (5) |
| 200 | Bioreactor |
| 205 | System for processing somatic plant embryos |
| 210 | Extraction of embryogenic clusters |
| 215 | Transfer of embryogenic clusters |
| 220 | Disperser |
| 225 | Transfer of dispersed embryogenic mass |
| 230 | Separator |
| 233 | Transfer of Immature embryogenic tissue |
| 235 | Transfer of separated embryos |
| 240 | Dilutor |
| 245 | Transfer of Diluted embryos |
| 247 | Sorter reservoir |
| 249 | Test section |
| 250 | Detector-Sorter-Orienting System |
| 255 | Transfer of oriented embryos |
| 260 | Deposition of oriented mature embryos in embryo receivers |
| 263 | Fluid and rejected embryos |
| 265 | Transfer of Accepted mature embryos |
| 270 | Germination |
| 280 | Nursery |
| 290 | Dilution fluid |
| 300 | Plate with embryo containers |
| 305 | Perforations in the plate |
| 310 | Rejection reservoir |
| 312 | Embryo collector |
| 313 | Step motor/switch |
| 315 | Linear actuator of the x-/y-table |
| 320 | Substrate |
| 325 | Cavity in substrate |
| 330 | Open space between embryo containers |
| 335 | Connectors between embryo containers |
| 340 | Embryo container |
| 345 | Perforations in embryo container |
| 350 | Narrow hole |
| 360 | length of the free jet |
| 365 | Outlet |
| 370 | Straight section of tube before outlet 365 |
| 375 | Flow direction of fluid and oriented embryos |
| 380 | Tube diameter |
| 381 | Encapsulating liquid |
| 382 | Encapsulating liquid delivery jet |
| 383a | Oriented embryo inside the delivery jet |
| 383b | Embryo inside an unstable delivery jet |
| 385 | Substantially stable delivery jet |
| 386 | Substantially unstable delivery jet |
| 387 | Vessel delivering the encapsulating liquid (tube) |
| 388 | Inner delivering tube |
| 401 | Segment of an axisymmetric channel |
| 402 | Segment of an axisymmetric channel |
| 403 to 440 | Dimensions according to Table 5 |
| 441 | Connector tube |
| 481 | Segment of a non-axisymmetric channel |
| 481a | Cross section of 481 |
| 482 | Segment of a non-axisymmetric channel |
| 482a | Cross section of 482 |
| 442 to 490 | Dimensions according to Table 6 |
| 501 | Fluid inlet |
| 502 | Inlet tube |
| 503 | Fluid outlet |
| 504 | Outlet tube |
| 505 | Reservoir tube |

TABLE 2-continued

List of designations pertaining to the Figures.

| | |
|---|---|
| 506 | Reservoir device |
| 507 | Intersection |
| 508 | Inlet valve (optional) |
| 509 | Outlet valve (optional) |
| 510 | Orientation detector |
| 511 | Reservoir tube detector (optional) |
| 512 | Outlet tube detector (optional) |
| 518 | Flow direction |
| 519 | Three-way intersection valve (optional) |
| 521 | Secondary destination plate (optional) |
| 522 | Secondary outlet tube (optional) |
| 523 | Secondary intersection (optional) |
| 524 | Liquid drainage (optional) |
| 530 | Inlet/outlet openings of the intersection valve |
| 531 | Intersection valve house |
| 532 | Intersection valve rotor |
| 533 | Intersection valve rotor flow channel |
| 534 | Diameter of inlet/outlet |
| 540 | x, y-movable table device (optional) |
| 541 | Device for x, y-moving the outlet tube (504) (optional) |
| 550 | Three way valve at secondary intersection (523) (optional) |
| 560 | Tube air inlet/outlet to reservoir device (optional) |
| 561 | Air inlet/outlet (optional) |
| 562 | Air filter (optional) |

TABLE 5

Figure 13:
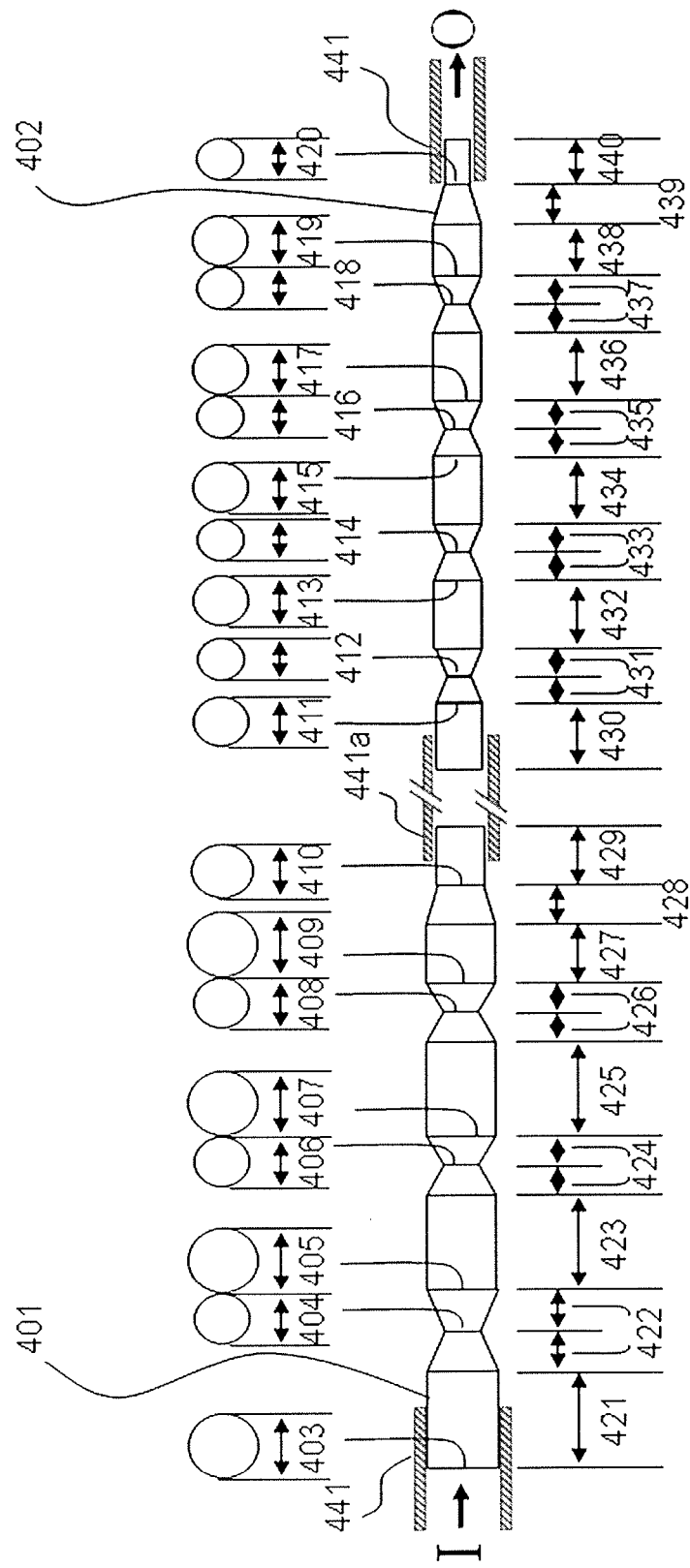
FIG. 13. Illustration of an axisymmetric disperser unit.

List of dimension designations pertaining to FIG. 13.

| Cross section position | Inner diameter [mm] | Preferred Inner diameter for Norway Spruce |
|---|---|---|
| (403) | 3.0-10.0 | 9.0-9.5 |
| (404) | 2.0-9.0 | 5.0-5.5 |
| (405) | 3.0-10.0 | 9.0-9.5 |
| (406) | 2.0-9.0 | 4.75-5.0 |
| (407) | 3.0-10.0 | 9.0-9.5 |
| (408) | 2.0-9.0 | 4.0-4.25 |
| (409) | 3.0-10.0 | 9.0-9.5 |
| (410) | 2.0-9.0 | 5.5-6.0 |
| (411) | 2.0-9.0 | 5.75-6.0 |
| (412) | 1.0-8.0 | 3.25-3.5 |
| (413) | 2.0-9.0 | 5.75-6.0 |
| (414) | 1.0-8.0 | 3.0-3.25 |
| (415) | 2.0-9.0 | 5.75-6.0 |
| (416) | 1.0-8.0 | 2.5-2.75 |
| (417) | 2.0-9.0 | 5.75-6.0 |
| (418) | 1.0-8.0 | 2.5-2.75 |
| (419) | 2.0-9.0 | 5.75-6.0 |
| (420) | 2.0-9.0 | 5.75-6.0 |

| Length on details | Length [mm] |
|---|---|
| (421) | 30.0 |
| (422) | 10.0 |
| (423) | 30.0 |
| (424) | 5.0 |
| (425) | 30.0 |
| (426) | 5.0 |
| (427) | 20.0 |
| (428) | 10.0 |
| (429) | 20.0 |
| (430) | 30.0 |
| (431) | 5.0 |
| (432) | 30.0 |
| (433) | 5.0 |
| (434) | 30.0 |
| (435) | 5.0 |
| (436) | 30.0 |
| (437) | 5.0 |
| (438) | 20.0 |
| (439) | 10.0 |
| (440) | 10.0 |

TABLE 6

Figure 14:
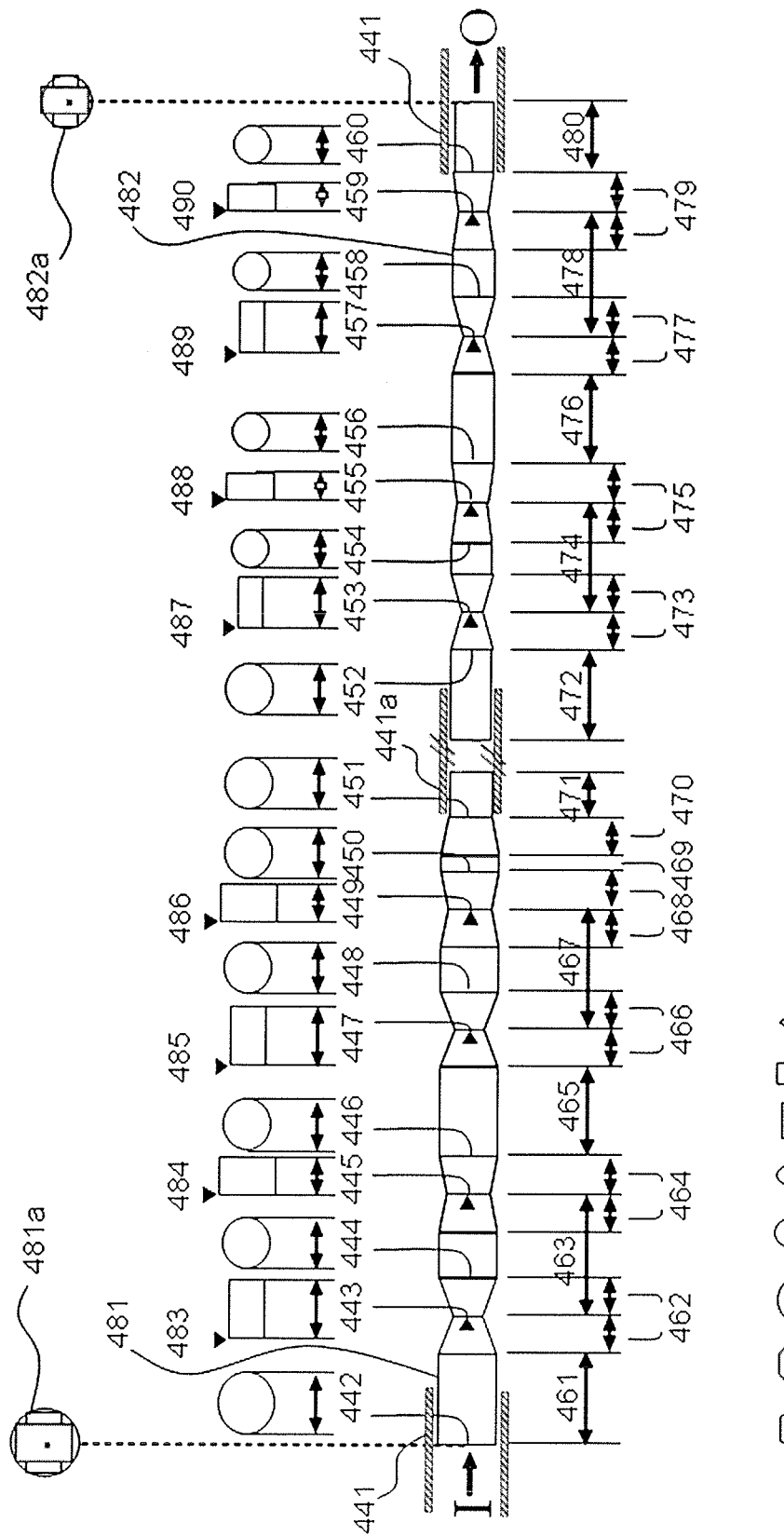
FIG. 14. Illustration of a non-axisymmetric disperser unit.
Figure 15:
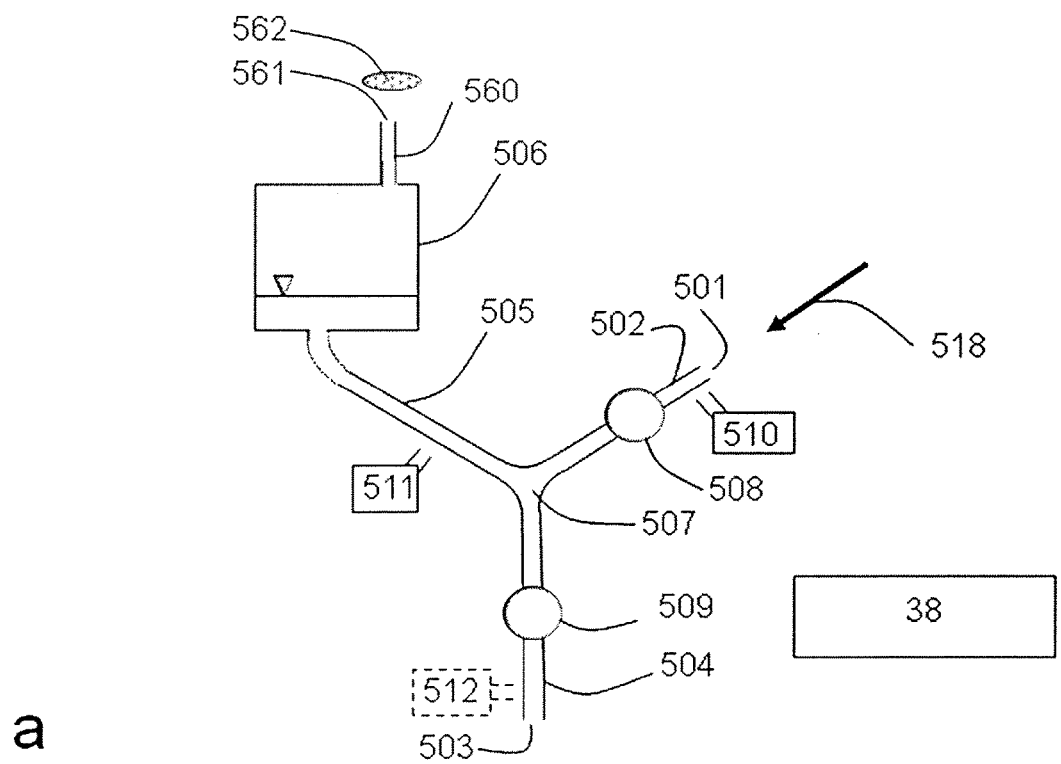
FIG. 15 a-f. Illustration of the detector-sorter-orienting unit.
Figure 15:
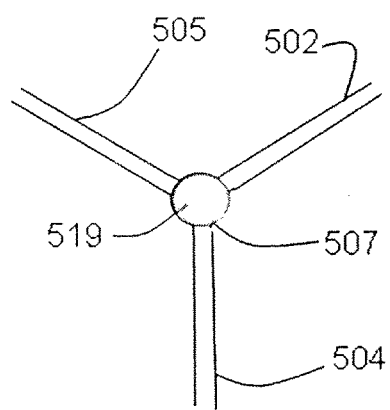
Figure 15:
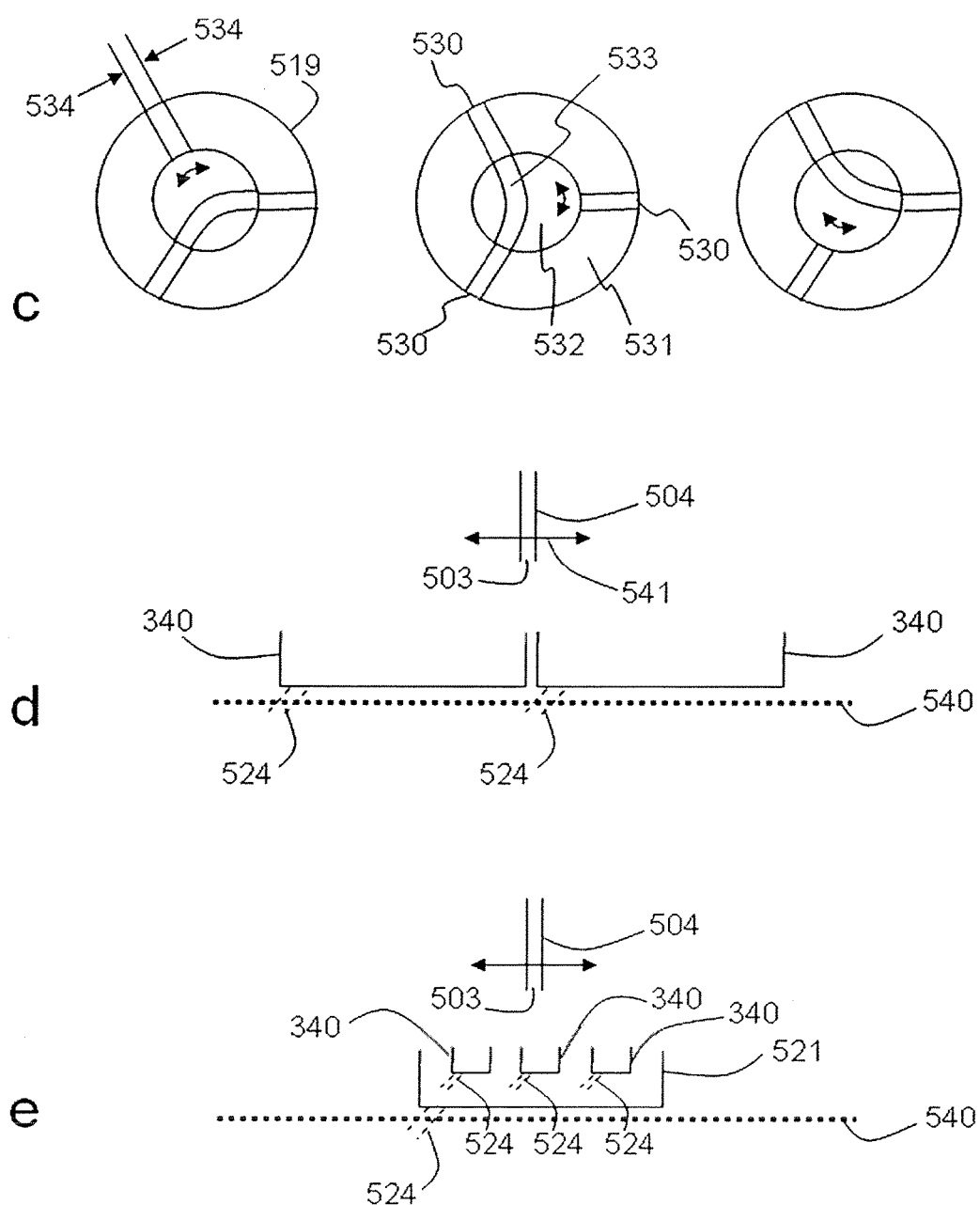
Figure 15:
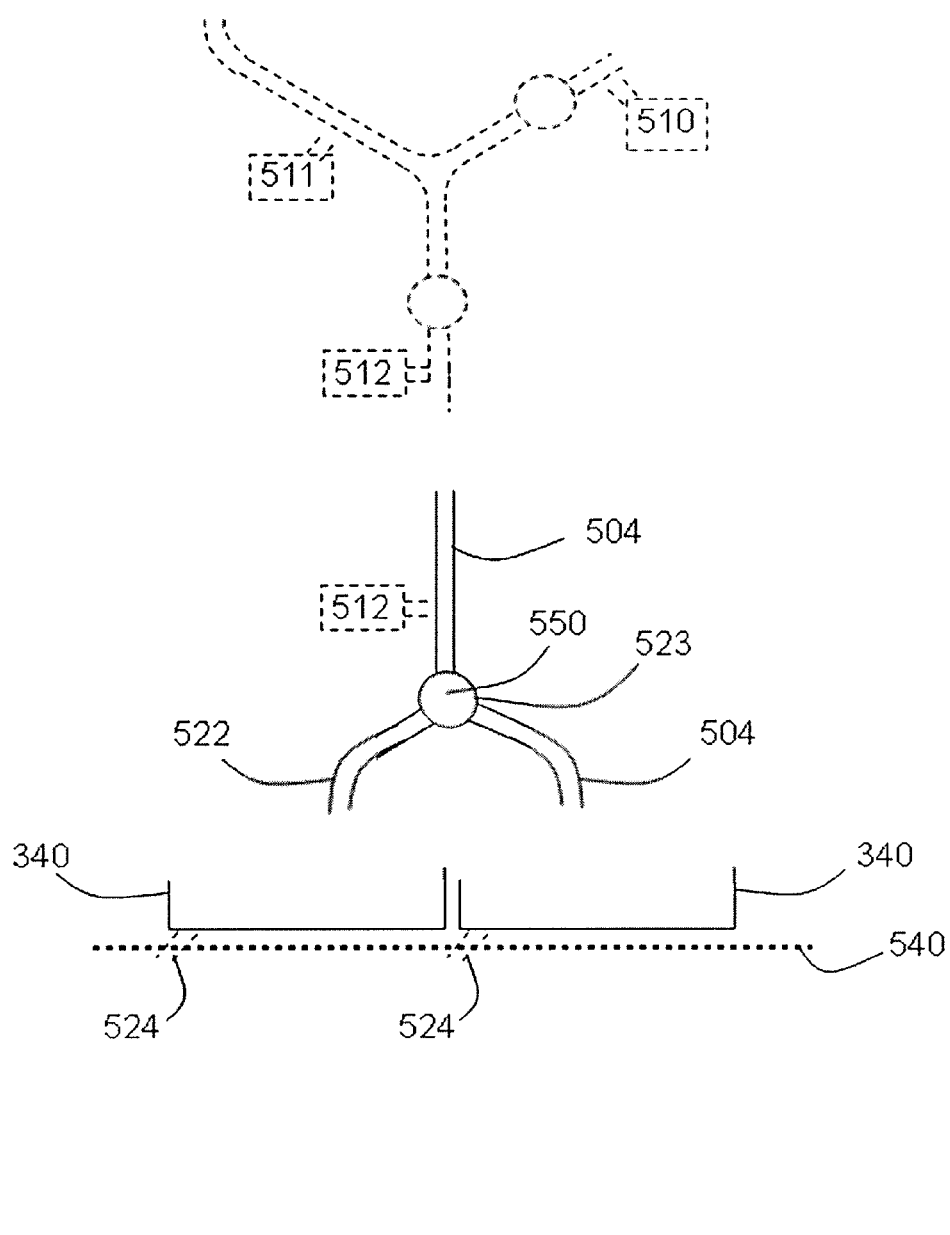

List of dimension designations pertaining to FIG. 14
Exemplified inner cross-section dimensions

| Shape of inner section | Inner dimensions [mm] | | Black arrow side [mm] (483)-(490) | | Width side [mm] | |
|---|---|---|---|---|---|---|
| | Alt. 1 | Alt. 2 | Alt. 1 | Alt. 2 | Alt. 1 | Alt. 2 |
| (442) circular | 9.5 | 9.5 | | | | |
| (443) Rectangular | | | (483) 5.0 | (483) 4.75 | 9.5 | 9.5 |
| (444) circular | 9.5 | 9.5 | | | | |
| (445) Rectangular | | | (484) 9.5 | (484) 9.5 | 5.0 | 4.25 |
| (446) circular | 9.5 | 9.5 | | | | |
| (447) Rectangular | | | (485) 5.0 | (485) 3.75 | 9.5 | 9.5 |
| (448) circular | 9.5 | 9.5 | | | | |
| (449) Rectangular | | | (486) 9.5 | (486) 9.5 | 5.0 | 3.5 |
| (450) circular | 9.5 | 9.5 | | | | |
| (451) circular | 6.0 | 6.0 | | | | |
| (452) circular | 6.0 | 6.0 | | | | |
| (453) Rectangular | | | (487) 3.5 | (487) 3.25 | 6.0 | 6.0 |
| (454) circular | 6.0 | 6.0 | | | | |
| (455) Rectangular | | | (488) 6.0 | (488) 6.0 | 3.5 | 3.25 |
| (456) circular | 6.0 | 6.0 | | | | |
| (457) Rectangular | | | (489) 3.5 | (489) 2.75 | 6.0 | 6.0 |
| (458) circular | 6.0 | 6.0 | | | | |
| (459) Rectangular | | | (490) 6.0 | (490) 6.0 | 3.5 | 2.75 |
| (460) circular | 6.0 | 6.0 | | | | |

SUMMARY OF THE INVENTION

In the first aspect, the invention provides a device for separating fluid-suspended embryos and immature embryogenic tissue from each other comprising:
  a) separator container (5), which during operation contains fluid having a density lower than the density of the embryos to be separated, said container being essentially cylindrical in shape, having an essentially flat bottom wall (6), an essentially vertical axis and comprising a fluid conduit (7) in communication with the inside of the container, located at the axial region of the bottom wall (6);
  b) means of inducing an axisymmetric rotating flow in the fluid relative to the bottom wall (6), whereby during operation:
    i) a viscous boundary layer (20) is created at the bottom wall (6);
    ii) a radial pressure gradient is created in the separator container (5);
  c) means of introducing the fluid-suspended embryos and immature embryogenic tissue to be separated into the separator container (5) at a location away from the bottom wall (6), whereby during operation:
    i) the embryos sediment faster than the immature embryogenic tissue;
    ii) the embryos enter the viscous boundary layer (20) while the immature embryogenic tissue remains substantially outside the viscous boundary layer (20);
    iii) the embryos entering the viscous boundary layer (20) are drawn into the axial region of the bottom wall (6) and into the conduit (7); and
  d) means of collecting embryos from said conduit (7); whereby the embryos collected are essentially separated from immature embryogenic tissue.

Preferably, the device of the first aspect is a device wherein the conduit (7) is placed and dimensioned such that embryos drawn into the axial region of the bottom wall (6) during operation enter into the conduit (7) by gravitational sedimentation.

Preferably, the device of the first aspect is a device wherein the means collecting embryos comprise means of collecting the embryos from the conduit (7) without substantially altering the volume of fluid in the container.

Preferably, the device of the first aspect is a device wherein the means of
removing the embryos from the conduit (7) without altering the volume of fluid in the container comprise a valve or a set of valves (36).

Preferably, the device of the first aspect is a device wherein
i) the device comprises means of draining fluid from said conduit (7), whereby during operation a sink vortex is created at the axial region of the bottom wall (6); and
ii) the means of collecting embryos comprise means of collecting the embryos from the sink vortex in the fluid drained from the conduit (7).

Preferably, the device of the first aspect is a device wherein the device is adapted for batchwise operation and further comprises means of collecting the embryos selectively during a time period after the sedimentation of the embryos has occurred but before the immature embryogenic tissue has had time to sediment.

Preferably, the device of the first aspect is a device wherein the device is adapted for continuous operation and further comprises a separator container (5) comprising a second outlet (25) at the top of the separator container (5) and means of feeding fluid into the separator container (5) at a rate exceeding the rate of fluid flow from the conduit (7), preferably by a factor in the range of 2-100, more preferably by a factor in the range of about 5-20.

Preferably, the device of the first aspect is a device wherein the second outlet (25) is implemented by means of a separator container (5) which is open at the top.

Preferably, the device of the first aspect is a device wherein the means of collecting embryos from the sink vortex comprise means of collecting the fluid exiting the conduit (7).

Preferably, the device of the first aspect is a device wherein the device additionally comprises means of replacing the fluid in the separator container (5).

Preferably, the device of the first aspect is a device wherein the device comprises means of draining fluid from the axial region of bottom wall (6) during operation, comprising a conduit extended from above or any other direction to the proximity of the axial region of the bottom wall (6).

The device of the first aspect may preferably comprise a separator container (5) having diameter in the range of 5-30 cm, more preferably 10-25 cm, 10-25 cm or 18-22 cm, most preferably about 20 cm.

The device of the first aspect may preferably comprise a fluid conduit (7) having an area of 0.01%-10%, more preferably 0.01-1%, even more preferably 0.1-0.15%, and most preferably about 0.125% of the area of the bottom wall (6).

The device of the first aspect may preferably comprise a means of inducing an axisymmetric rotating flow resulting in a rotational speed in the range of 5-1200 rpm, more preferably 30 to 360 rpm in the fluid.

The device of the first aspect may preferably comprise a means of inducing an axisymmetric rotating flow comprising a rotating disk- or cylinder-shaped object.

The device of the first aspect may preferably comprise a means of introducing embryos and immature embryogenic tissue located at an axial location near the surface of the fluid present during operation.

The device of the first aspect may preferably comprise a means of maintaining a static fluid height being 0.1-10 times, more preferably 0.8-2 times the diameter of the separator container (5).

In a second aspect of the invention, a method of separating fluid-suspended embryos from immature embryogenic tissue is provided, comprising the steps of:
a) providing a suitable separator container (5), said container containing fluid having a density lower than of the embryos to be separated, being essentially cylindrical in shape, having an essentially flat bottom wall (6) and an essentially vertical axis;
b) inducing an axisymmetric rotating flow in the fluid relative to the bottom wall (6), thus:
i) creating a viscous boundary layer (20) at the bottom wall (6); and
ii) creating a radial pressure gradient in the separator container (5);
c) introducing the fluid-suspended embryos and immature embryogenic tissue to be separated into the fluid present in the separator container (5) at a location away from the bottom wall (6), thus:
i) sedimenting the embryos faster than the immature embryogenic tissue;
ii) allowing the embryos to enter the viscous boundary layer (20) while not allowing the immature embryogenic tissue to enter the viscous boundary layer (20);
iii) drawing the embryos entering the viscous boundary layer (20) into the axial region of the bottom wall (6); and
d) collecting embryos from said axial region of the bottom wall (6),
whereby the embryos collected are essentially separated from immature embryogenic tissue.

Preferably, the device provided in step a) above further comprises a conduit (7) in communication with the fluid in the container at the axial region of the bottom wall (6) during operation and the method further comprises the steps of creating a sink vortex at the axial region of the bottom wall (6) by draining fluid from said conduit (7); and collecting embryos from said axial region of the bottom wall (6) in the fluid drained from the conduit (7).

Preferably, the device provided in step a) above further comprises a suitable separator container (5) further comprising a conduit (7) in communication with the fluid in the container at the axial region of the bottom wall (6) during operation, wherein the conduit (7) is placed and dimensioned such that embryos drawn into the axial region of the bottom wall (6) during operation enter into the conduit (7) by gravitational settlement; and the method further comprises collecting embryos from said conduit (7). More preferably, the method further comprises the step of modulating the sedimentation velocity of the embryos in the conduit (7) by means of inducing fluid flow through the conduit (7) into the separator container (5).

The method of the second aspect may preferably be adapted for batchwise operation and further comprises selectively collecting the embryos during a time period after the sedimentation of the embryos has occurred but before the immature embryogenic tissue has had time to sediment. The method of the second aspect adapted for batchwise operation may preferably additionally comprise the step of replacing the fluid in the separator container (5) after processing a batch of embryos with fresh fluid.

The method of the second aspect may preferably be adapted for continuous operation such that it comprises feeding fluid into the separator container (5) at a rate exceeding the rate of fluid flow from the conduit (7), preferably by a factor in the range of 1.1-1000, more preferably 2-100, even more preferably 2-50, 2-30, 3-20 or 5-15, most preferably about 10.

The method of the second aspect may preferably comprise that the collection of embryos is performed by allowing the embryos to enter the fluid exiting the conduit (7), and collecting the fluid containing embryos.

In a third aspect, a method for depositing a fluid-suspended plant somatic embryo in an embryo receiver while maintaining the orientation of the embryo is provided, comprising the steps of:
  i) Providing a suitable embryo receiver (340) with means of draining fluid (345), (350) from the receiver;
  ii) Providing a flow channel dimensioned such that the embryos may travel with the fluid flowing though the channel but are restricted to travelling either in a crown-first or crown-last orientation by dimensional constraints, said flow channel having an outlet (365) wherein said flow channel comprises a flow channel section immediately upstream of the outlet (365) having a straight section (370) with length at least equal to the largest cross-sectional inside dimension of the flow channel (380);
  iii) Placing an embryo (preferably an embryo having the desired orientation) in the flow channel; and
  iv) Forming a free jet (385 and 386) of fluid emanating from the outlet (365), aligning said free jet with the embryo receiver (340) and depositing the embryo from the flow channel into the receiver by using said free jet as a carrier means.

The method of the third aspect preferably further comprises the steps of:
  i) Determining the orientation of the embryo in the flow channel;
  ii) In case the orientation does not match the desired orientation, directing the embryo away from the embryo receiver (340); and
  iii) In case the orientation does match the desired orientation, directing the embryo into the embryo receiver (340).

In a fourth aspect of the invention, a device for depositing fluid-suspended plant somatic embryos while maintaining the orientation of the embryo is provided comprising:
  i) a flow channel dimensioned such that the embryos may travel with fluid flowing though the channel but are restricted to travelling either in a crown-first or crown-last orientation by dimensional constraints, said flow channel emanating to an outlet (365);
  ii) an embryo receiver (340); and
  iii) means of forming a free jet of fluid emanating from the outlet (365), wherein the free jet is during operation aligned with an embryo receiver (340) thus allowing embryos suspended in the fluid to be deposited in the embryo receiver;
  wherein the means of forming a free jet comprise a flow channel section immediately upstream of the outlet (365) having a straight section (370) with length at least equal to the largest cross-sectional inside dimension of the flow channel (380).

The device according to the fourth aspect may preferably be designed such that the length of the straight section is at least 10 times the largest cross-sectional inside dimension of the flow channel (380).

The device according to the fourth aspect may preferably be designed such that the outlet tip (365) is positioned during operation one to three flow channel diameters from the embryo receiver (340).

The device according to the fourth aspect may preferably be designed such that the embryo receiver (340) has an opening for depositing the embryo having a smallest dimension of at least 10% larger than the largest cross-sectional diameter of the embryo (103) to be deposited.

The device according to the fourth aspect may preferably further comprise means stabilising the jet delivering the embryos comprising means of encapsulating (387) the jet delivering the embryos in another fluid jet with a larger diameter.

In a fifth aspect of the invention, a system for processing plant embryos suspended in a fluid is provided, comprising a separator device (230) according to the first aspect of the invention, and at least one of the following:
  a) a disperser unit (220) to disperse the embryos and the embryogenic tissue suspended in a fluid, located upstream of the separator device, and optionally a bioreactor (200), as embryo source, located upstream of the disperser unit (220);
  b) orientation and sorting unit (250) for orienting and sorting the embryos suspended in a fluid, located downstream of the separator device (230); and optionally a deposition device (260), preferably located downstream of the orientation and sorting unit (250).

In a sixth aspect of the invention, a system comprising a deposition device (260) according the fourth aspect of the invention, and one or more of the following:
  a) a disperser unit (220) to disperse the embryos and the embryogenic tissue suspended in a fluid, and optionally a bioreactor (200), as embryo source, located upstream of the disperser unit (220);
  b) a separator device (230) according to the first aspect of the invention, located downstream of the disperser unit (220);
  c) orientation and sorting unit (250) for orienting and sorting the embryos suspended in a fluid, located downstream of the separator device (230) and upstream of the deposition device (260).

DETAILED DESCRIPTION OF THE INVENTION

The somatic embryos produced on solid or liquid medium in petri dish or biorectors are initially glued together by immature embryogenic tissue into embryogenic clusters or lumps normally up to 50 mm or sometimes larger diameter. Prior art teaches methods of picking individual embryos either manually by tweezers or automatically by conveyer belts and robotic arms and placing the embryo in an artificial seed. Prior art does not teach how to rapidly and efficiently breakup the embryogenic clusters and separating the mature embryos and placing the mature and viable embryos each in the right orientation in an individual container, which could be an artificial seed or otherwise, in a matter of seconds. To provide efficient means for large-scale production of plants from somatic plant embryos, an automated means for rapidly and inexpensively separating the mature embryos from the said embryogenic clusters and rapidly depositing the mature embryos in the correct orientation into an appropriate substrate for germination is required. To do so requires four major operational steps, as disclosed herein.

Firstly, a gentle dispersion of the clusters of somatic embryos into individual embryos detached from the immature embryogenic tissue, which is advantageously performed while suspended in a liquid medium.

Secondly, the process involves segregating and separating the embryos from the immature embryogenic tissue now dispersed but still mixed together in the liquid medium. The second step is useful, for example, in order to provide an optically clear access to the embryos suspended in a transparent liquid medium without the presence of the embryogenic tissue. The need for such optical access is to establish the level of maturity and suitability of the embryos for germination and plant production.

Thirdly, the process involves identification of the orientation of the mature embryos prior to deposition and correction of an undesired orientation, which is done while the embryos are still suspended in liquid medium.

Fourthly, the process involves deposition of the mature embryos with the right orientation into an appropriate substrate for germination and plant formation.

Effective combination of the above four steps in a fluid dynamics-based automated system capable of rapidly and efficiently transporting the embryos through each step, as disclosed herein, provides a means for efficient large-scale production of plants from somatic embryos.

Figure 10:
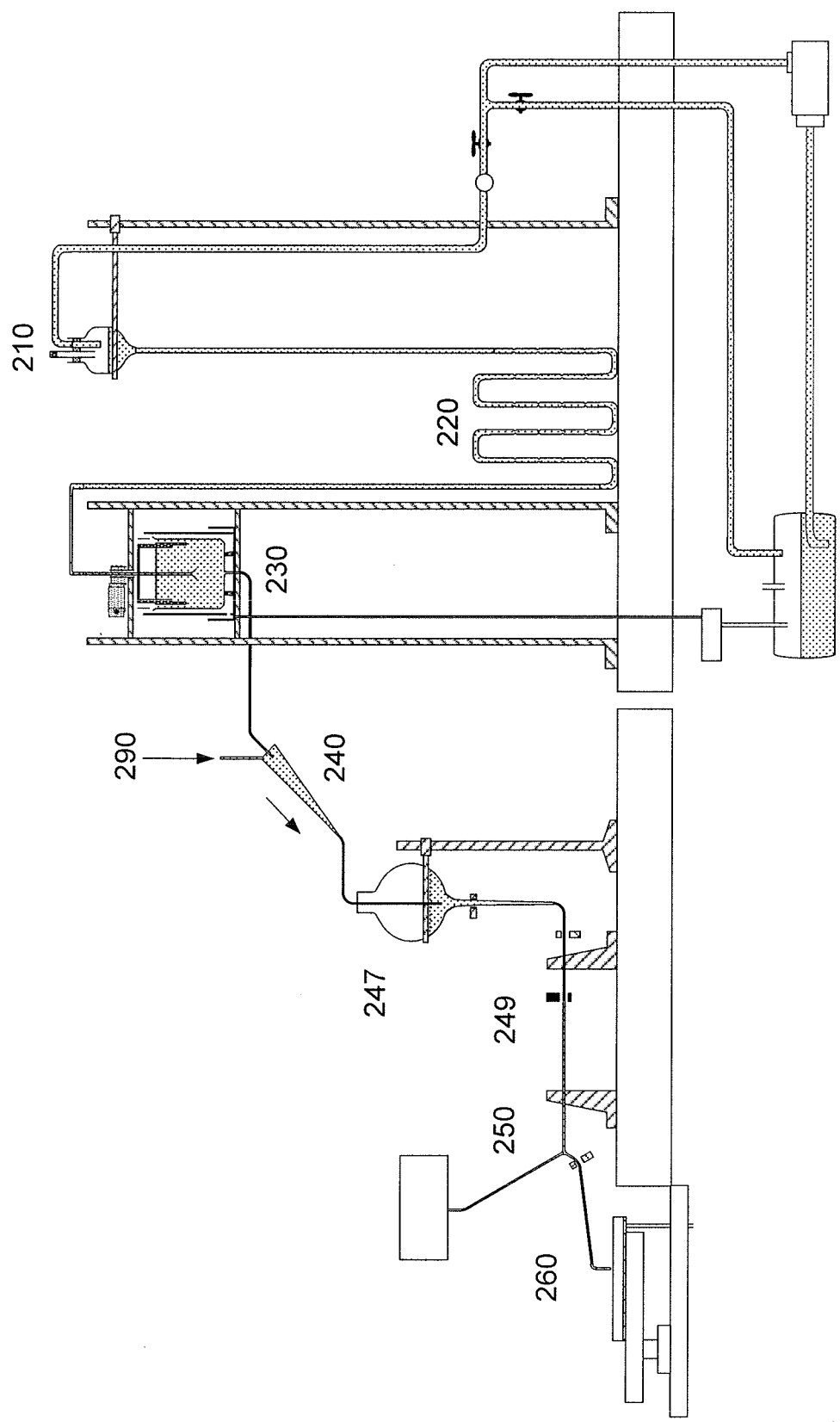
FIG. 10. Illustrates a fully integrated automated system comprising units of the invention as verified in the experimental part.

An embodiment of the fluid dynamics-based automated system for rapid and efficient dispersion, separation, sorting and orientation, and deposition of plant embryos in a substrate for germination is disclosed in FIG. 10. The automated system involves several innovative steps, as disclosed, in the order of process outlined in the FIG. 10, and outlined herein:
  1. The disperser unit (220) by reference to patent application PCT/US09/39981, and also disclosed herein,
  2. The separator unit (230), as disclosed herein,
  3. The detector and orienting unit (250) by reference to patent application PCT/US09/39982, and also disclosed herein
  4. The deposition device for germination (260), as disclosed herein.

1. Disperser Unit

Detailed description of a disperser unit for means to disperse the embryogenic cluster in liquid medium as disclosed in patent application PCT/US09/39981 is hereby incorporated by reference in its entirety.

Disperser Unit of the System

PCT/US09/39981 relates to methods and devices for gently dispersing clusters of somatic plant embryos into individual embryos and immature embryogenic tissue useful in the system of the invention.

A method of dispersion of clusters of plant embryos suspended in a liquid medium into individual plant embryos is disclosed in PCT/US09/39981, said method including at least one dispersion sequence, which comprises the following steps:
  i) subjecting the clusters of embryos to fluid dynamics forces causing axially extensional strain and radially compressional strain;
  ii) subjecting the clusters of embryos to fluid dynamics forces causing axially compressional strain and radially extensional strain from fluid dynamics forces;
  repeating said steps in sequence until the individual embryos are separated from each other.

Preferably, the strength of the extensional and compressional strains increases with each repeated sequence.

A disperser for separating individual embryos contained in clusters of embryos is also disclosed in PCT/US09/39981, comprising a flow channel including at least one constriction, such that clusters of embryos flowing through the flow channel are first subjected to axially extensional strain and radially compressional strain, and then to axially compressional strain and radially extensional strain from fluid dynamics forces.

Preferably, the flow channel comprises at least two constrictions, each constriction having an inner diameter, which is equal to or smaller than the inner diameter of the constriction immediately up-stream of thereof.

Preferably, the flow channel includes an intermediate portion having a constant cross-section, between each constriction.

Preferably, each intermediate portion has an inner diameter, which is equal to or smaller than the inner diameter of the intermediate portion immediately up-stream of thereof.

Preferably, each intermediate portion may have a length at least equal to the clusters of embryos to be dispersed. Preferably, the length of each intermediate portion is in the interval from 2.5 mm to 60 mm, more preferably from about 5 mm to about 30 mm. The number of constrictions may be 3-100, preferably 5-20, most preferably about 10. Preferably, the constrictions have a cross-sectional area in the interval from 0.75 to 1300 mm$^2$, more preferably in the interval from 3 to 32 mm$^2$.

The flow channel may have axisymmetric cross-section. The flow channel may have an essentially circular or oval cross-section.

At least part of the flow channel may have a non-axisymmetric cross-section such as a rectangular cross-section. The cross-section of each non-axisymmetric constriction, having a maximal dimension, may preferably be oriented such that the maximal dimension of each constriction is rotated, preferably at least 30°, more preferably about 90° in relation to maximal dimension of the next non-axisymmetric constriction in sequence. The cross-section of each constriction may represent a rectangle, having a first and a second side, wherein the first side is longer than the second side, and the constrictions are oriented such that first side of each constriction is perpendicular to the first side of the next constriction in sequence having a rectangular cross-section.

The advantages of the method and the device of dispersion disclosed in PCT/US09/39981 include:
(1) Not requiring moving parts, and therefore being robust
(2) Being naturally applicable to a continuous flow system thereby not requiring operation in batch mode
(3) Being gentle to the embryos
(4) Being fast; the dispersion using the device requires only a few seconds to disperse hundreds of embryos
(5) The device being compact and completely enclosed allows easy sterilization.

2. Separator Unit

Device for Segregating and Separating Somatic Embryos from Embryogenic Tissue

Once an embryogenic cluster is dispersed in liquid, it creates a mixture of mature embryos, immature embryos and immature embryogenic tissue suspended in liquid. The somatic embryos have to be segregated and separated from the immature embryogenic tissue for further processing and planting. In an automated system it is highly desirable to perform this separation process rapidly, efficiently and without causing any interruption to the continuous operation of the system. Such a separator device of the invention is disclosed herein.

The separator device and method of the invention takes advantage of the difference in the drag coefficient of embryos as opposed to the immature embryogenic tissue (hereinafter "tissue" or "embryogenic tissue") in the suspension, to provide a device and method of separating somatic embryos from embryogenic tissue.

General Construction and Operation of the Device

To facilitate the theoretical discussion that will follow a brief general description of a device of the invention is presented below.

The separator device of the invention has a preferably essentially cylindrical separator container (5) containing fluid medium during operation, and means of inducing an axisymmetric rotating flow in the fluid within the separator container (5). There is a bottom wall (6) which is preferably essentially flat. The fluid medium has a density that is lower than that of the embryos and tissue to be separated. The fluid medium may preferably be water.

The fluid medium inside the separator container (5) is induced to rotate (in relation to the bottom wall (6)) around the axial centre of the separator container (5), with essentially homogenous rotational velocity within the entire separator container (5), except near a thin boundary layer forming on the surface of the bottom wall (6) where the rotational velocity rapidly approaches zero at the bottom wall (6). Due to the rotation of the fluid, the pressure increases along the radial direction everywhere in the separator container (5), including inside the thin boundary layer at the bottom wall (6), by substantially homogenous amount. More precisely, the pressure increases in the radial direction such that the rate of change of pressure with respect to radial distance from the centre axis (10) is independent of the axial location and quadratically dependent on rate of rotation and linearly dependent on radial distance from centre axis.

There is a conduit (7) at the axial region (centre) of the bottom wall (6) from which somatic embryos can be removed and collected.

The embryos mixed with immature embryogenic tissue (hereafter tissue) are introduced into the fluid in the separator container (5), at sufficient distance away from the bottom wall (6). The embryos and tissue quickly entrain and disperse in the rotating fluid with the centrifugal force pushing them outward and the inward pressure force pushing them inward. The two forces counteract each other and the embryos and tissue eventually find a balanced orbit to rotate around. However, the embryos will sediment faster than the tissue while rotating. The tissue having a larger relative drag will remain substantially more entrained and suspended rotating along the balanced orbit and exhibits a much lower rate of sedimentation. Upon sedimenting towards the bottom, the embryos enter said boundary layer while the tissue remains substantially outside the boundary layer for reasons elaborated below. Upon entering the boundary layer, the rate of rotation of the embryos will slow down substantially. The inward pressure force, however, remains substantially the same. Thus, for embryos inside the boundary layer (20), the inward pressure force becomes dominant over the centrifugal force pushing the embryos towards the centre; consequently the embryos are pushed into the axial region of the bottom wall (6) and into the conduit (7) once they have reached the boundary layer. The embryos may then be collected from the conduit (7) using a collection means, e.g. by collecting fluid exiting the conduit (7) (see more detailed description of collection means below).

The tissue having a larger surface to volume ratio than the embryo is under higher drag and therefore, substantially more susceptible to being entrained in the primary rotating flow than the embryo. When the tissue approaches the boundary layer at the bottom of the container, it is easily swept back into the rotating flow due to the higher drag.

A key feature of the invention is the creation of the thin boundary layer on the bottom wall (6) surface beneath an axisymmetrically rotating fluid such that the embryos can sediment and enter the boundary layer while the tissue having a larger drag cannot enter the boundary layer because of repeated entrainment in the primary rotating flow. The (i) segregation of the embryos from the tissue at the boundary layer due to drag differential and (ii) the imbalance of the pressure force relative to the centrifugal force inside this boundary layer are important features that in combination provide unique and effective means to rapidly segregate and separate the embryos from tissue. Further (iii) presence of a sink vortex may be a useful feature of the invention, as further elaborated below. Utilization of this combinatorial effect is one feature that clearly distinguishes the device of the invention from known devices such as hydroclones or cyclone cleaners.

Flow-Dynamic Considerations with Regard to the Method and the Device for Separating Somatic Embryos from Embryogenic Mass The invention is based on creating a combination of effects that result in segregating the embryos from the immature embryogenic tissue.

Said effects comprise:
a) creating a viscous boundary layer at the bottom wall (6), which is achieved by inducing axisymmetric rotating flow in the fluid (in relation to the bottom wall (6)) using rotation means (18);
b) directing only the embryos to enter the said viscous boundary layer, which is achieved by that the tissue has a much lower rate of sedimentation and much higher drag;
c) creating a radial pressure gradient in the separator container (5), which is achieved by the centrifugal effect of the rotation;
d) optionally, creating a sink vortex near the centre of the bottom wall (6), which is achieved by draining fluid from the conduit (7) during operation.

Consequently embryos will be separated from the tissue and directed into the axial region (centre) of the bottom wall (6) and into the conduit (7), where they may subsequently be collected using a collection means, e.g. simply by collecting fluid exiting the conduit (7). The theoretical basis and practicalities for said effects is discussed below.

When the rotation means is not active, a Free vortex (see Definitions) can be created in the separator container (5) by draining fluid through the conduit (7). In this case, the free-surface of the fluid will be nearly levelled except near the centre where the fluid surface bends sharply downward. The sink flow creates a Free vortex throughout the separator container (5) and forms a sink boundary layer at the bottom surface. The fluid particles outside the sink boundary layer move along a nearly circular pathline created by balance of the outward direction centrifugal force on said fluid particles and the inward direction force due to radial pressure gradient in the flow in the separator container (5). The fluid particles inside the sink boundary layer rotate at relatively slower rate of rotation than the fluid particles outside the said layer; consequently, the fluid particles inside the sink boundary layer enter the sink due to lack of sufficient centrifugal force to keep said fluid particles in a nearly circular pathline as compared to the fluid particles outside the sink boundary layer. The inward force due to the pressure gradient wins over the outward centrifugal force.

The sink vortex is very efficient in capturing and draining the particles that are close to the centre, as the angular velocity increases rapidly as the particle moves toward the centre. However, in a sink vortex, the fluid particles not near the centre experience a slow moving vortex with decreasing angular velocity. Recall, outside the singularity at the centre, the angular (or tangential) velocity, defined as $v_\theta$, in a sink vortex decreases nearly as 1/r where r is the radius from the centre axis (10). Therefore, the flow is moving very slowly as moving away from the centre. This slow motion, allows the embryos and the immature embryogenic tissue to sediment to the sink boundary layer and drain into the conduit (7) together.

A key to this invention is to create a flow condition to separate the embryos from the immature embryogenic tissue prior to them entering the conduit (7).

Combination of Free and Forced Vortex

This may be achieved by combining the above effects of a Free vortex with the effects of a Forced vortex in a fluid-filled separator container (5) by:
a) creating a Free vortex by draining fluid from the conduit (7); and simultaneously
b) creating a Forced vortex by inducing axisymmetric rotating flow in the fluid using a rotation means (18).

Key phenomena arising from the combination of the Forced vortex and the Free vortex are explained in the following paragraphs.

In essence, certain embodiments of the invention take advantage of the common feature of the two vortex flows, which is the formation of a relatively thin viscous boundary layer at the bottom wall (6) of the separator container (5).

The shear stress exerted on the liquid by the rotation means (18) creates a Forced vortex superimposed on the Free vortex of the sink flow. Recall in the Forced vortex, where the fluid rotates nearly in solid-body rotation, the vorticity $\zeta_z$ is constant and the angular velocity is given by $v_\theta = 0.5 r \zeta_z$. Therefore, the angular velocity increases linearly with r as moving away from the centre. Near the centre, the flow is governed largely by the Free vortex of the sink flow, where away from the centre, the flow is primarily governed by the Forced vortex creating the ideal situation to control the movement of the embryos and the immature embryogenic tissue in a desired manner. The fluid rotating around the central axis (10) with a centripetal acceleration in the −r direction feels a (reactive) centrifugal force in the +r direction. If the said centrifugal force is balanced by the positive radial pressure gradient, defined by $$\frac{\partial p}{\partial r}$$

exerting a force on the particle toward the centre of the rotation (that is in the −r direction), then a buoyant particle will rotate around the centre axis (10) indefinitely in a circular path.

As the embryos and the immature embryogenic tissue material have a density greater than the fluid medium used (e.g. water), upon introduction into the separator container (5), they move generally outward into the flow field with increasing angular velocity in now the Forced vortex flow. The immature embryogenic tissue having a higher relative fluid drag force compared to the embryos, become more entrained into the rotating fluid than the embryos. Therefore, the embryos follow a spiral pathline around the separator container (5) and gradually toward the bottom wall (6), while the immature embryogenic tissue also takes on a spiral path but with a much slower settlement velocity. Because the embryogenic tissue is relatively larger in surface area to volume ratio, it will not enter the thin boundary layer as it easily gets entrained back into the primary rotating flow. In effect, the embryos enter the viscous boundary layer at the bottom in relatively short time; order of seconds or less, where the immature embryogenic tissue continues to get re-entrained back in the primary flow because of its larger surface area to volume ratio.

Once the embryos are inside the boundary layer, their angular velocity is reduced substantially while the positive radial pressure gradient remains substantially the same forcing the embryos inward towards the centre and into the sink vortex region. Once in the sink vortex region, the embryos may be collected, e.g. in the fluid entering the conduit (7).

Forced Vortex with Zero or Negligible Free Vortex

As outline above, a combination of a Free and a Forced vortex can be used to create flow conditions for separating embryos from embryogenic mass.

There is a reciprocal relation between the rate of liquid drainage through the conduit (7) and the purity achieved. By "purity" in this context is meant the effectiveness of separation of the immature embryogenic tissue from the embryos; higher purity means less embryogenic mass per embryo.

The lower the rate of liquid drainage through the conduit (7) (down to and including zero flow) the higher the purity achieved. Thus, in certain embodiments, it may be preferable that the Free vortex (sink vortex) is completely or substantially absent, to facilitate achieving high purity.

In absence of a sink vortex, the physical process due to rotation of the fluid inside the separator container (5), i.e. the boundary layer formation at the bottom plate (6), and the entrapment and inward pressure on the embryos to migrate toward the axial center of the separator container (5) inside the boundary layer at the bottom plate (6) remain exactly the same.

The difference from eliminating the sink vortex (with zero or almost zero liquid drainage) is that the embryos do not enter conduit (7) by a combination of fluid convection and gravitational settlement, but by gravitational settlement alone.

In other words, the mechanisms outlined above will force the embryos to the axial region of the bottom plate (6). Once the embryos reach the axial center of the bottom plate (6), where the angular (azimuthal) and radial fluid velocity is essentially zero, if the drainage rate and the axial velocity are also zero, then this center point is just a 'stagnation' point, and the embryo will have enough time at the center to settle into the conduit (7). Once inside the conduit (7), the embryo will settle gradually (e.g. ~10 cm per second for the embryos used the experiments).

However, the speed of separation gets slower with lower rates of liquid drainage through the conduit (7). Thus, in applications requiring high speed of separation, the combination of Free and Forced vortex may be preferred.

Viscous Boundary Layer

A feature of great interest is the thin axially-symmetric viscous boundary layer forming at the bottom wall (6) of the separator container (5). The viscous boundary layer is referred to a layer of fluid from the surface of the bottom wall (6) at z=0 to the region designated as the edge of the boundary layer (20) at z=δ where the fluid velocity becomes substantially the same as the Forced vortex. In this flow, the boundary layer thickness is substantially dependent on the fluid kinematic viscosity and the rate of rotation of the rotation means (18). One can get a good approximation of the boundary layer flow at the bottom of the separator container (5) by considering the momentum conservation for Newtonian viscous fluid flow (Navier-Stokes equations) for axisymmetric solid-body rotation of fluid above a stationary flat plate. The solution to the said flow is provided in the fluid mechanics literature (e.g., H. Schlichting, Boundary Layer Theory, McGraw Hill Series in Mechanical Engineering, 1979) and will not be reproduced here. We use the same solution to provide a good approximation to the flow inside the separator container (5) due to the rotation of the rotation means (18). This solution is valid in the boundary layer at the bottom wall (6) except at the centre and the outer edge near the solid wall of the separator container (5). One of the important aspects of the invention is based on the pressure gradient, $$\frac{\partial p}{\partial z},$$

inside the boundary layer being substantially negligible considering a sufficiently thin layer. In other words, the radial pressure gradient inside and outside of the boundary layer will be substantially the same, as given by $$\frac{\partial p}{\partial r} = \rho r \varsigma^2$$

where $\varsigma$ is the rate of rotation of the fluid medium. It is clear that this quantity is positive everywhere in the fluid in the container and therefore, the pressure increases with distance from the central axis of the separator container (5).

The increase in pressure with radius r results in formation of a parabolic variation in liquid height at the free surface of the fluid medium. Substantially the same radial pressure gradient exists inside the boundary layer forcing the fluid to move away from the walls of the separator container (5) and towards the central axis of the separator container (5). The magnitude of the pressure inside the boundary layer depends on the height of the fluid inside the separator container (5).

The height of the fluid in the container during operation (54) should be about the same as the diameter (51) of the container, preferably the height is 0.6-1.4 times the diameter, more preferably 0.8-1.2 times. Deviations from the ideal fluid height during operation may be tolerable but would result in suboptimal operation.

However, the pressure gradient and consequently the fluid velocity inside the boundary layer are dependent on the variation in the height of the fluid with respect to radius, and not the amount of liquid inside the separator container (5). As the rate of rotation increases, the pressure gradient increases and the inward velocity of the fluid and the entrained embryos in the boundary layer towards the centre increases. However, the boundary layer thickness, given by $\delta = 8\sqrt{v/\varsigma}$, decreases with increase in rate of rotation to a point where the thickness becomes less that the size of an embryo. The efficiency of the invention to separate the embryos from the immature embryogenic tissue is dependent on several parameters that will be discussed below. A key parameter is the speed with which the embryos can be directed into the axial region of the bottom wall (6) where they can be collected.

Some of the important parameters in this respect are the boundary layer thickness, $\delta$, the radial component of velocity, $v_r$, the ratio of the angular velocity to the radial velocity, $$\frac{v_\theta}{v_r},$$

as well as the axial velocity, $v_z$. Here we shall provide some quantitative values for each of these parameters based on rate of rotation and radial position. Although this information can be provided in a general form by giving the appropriately scaled quantities based on the similarity variables in the boundary layer equations, for the purpose of providing a specific example for a preferred embodiment in this section, we shall provide the results in dimensional form and based on specific preferred devices. Based on the teachings contained herein, the skilled person will be able to construct a functional separator device with parameters optimized for the specific type of embryos to be separated, as well as other relevant considerations.

Effects of Rate of Rotation

The separator container being used as a non-limiting exemplary embodiment has a diameter of 200 mm (51) and the exemplary liquid height is 200 mm (54). Using this exemplary separator container, we shall illustrate the effect of the rate of rotation of the fluid, in the units of rotation per minute (rpm), on the boundary layer thickness and the flow inside the boundary layer. Table 3 provides the values of the radial, axial and angular components of the fluid velocity and the ratio of the radial to axial and angular velocity inside the boundary layer from the bottom wall (6) at z=0 to 3 mm for rate of rotation 15 rpm at radial position r=7 mm. The boundary layer thickness for this case is 6.38 mm where by definition $v_\theta$ is about 98% of the free-stream angular velocity of about 110 mm/s.

TABLE 3

Radial, axial and angular components of the fluid velocity and the ratio of the radial to axial and radial to angular velocity inside the boundary layer from the bottom wall at z = 0 to the edge of the boundary layer at z = 6.4 mm for rate of rotation = 15 rpm at radial position r = 7 mm.

| z (mm) | $v_r$ (mm/s) | $v_z$ (mm/s) | $\frac{v_r}{v_z}$ | $v_\theta$ (mm/s) | $\frac{v_r}{v_\theta}$ |
|---|---|---|---|---|---|
| 0.0 | 0 | 0.00 | | 0.0 | |
| 0.4 | 0.0 | 0.24 | −157 | 42.2 | −0.91 |
| 0.8 | −38.3 | 0.78 | −67 | 80.9 | −0.65 |
| 1.2 | −52.6 | 1.38 | −36 | 111.4 | −0.44 |
| 1.6 | −49.4 | 1.88 | −19 | 131.1 | −0.28 |
| 2.0 | −36.1 | 2.19 | −9 | 139.9 | −0.14 |
| 2.4 | −19.4 | 2.32 | −2 | 139.8 | −0.03 |
| 2.8 | −4.0 | 2.29 | 3 | 133.9 | 0.05 |
| 2.8 | 7.3 | 2.29 | 3 | 133.9 | 0.05 |
| 3.2 | 13.5 | 2.42 | 6 | 125.5 | 0.11 |
| 3.6 | 15.1 | 2.01 | 8 | 117.0 | 0.13 |
| 4.0 | 13.3 | 1.84 | 7 | 110.1 | 0.12 |
| 4.4 | 9.7 | 1.71 | 6 | 105.7 | 0.09 |
| 4.8 | 5.5 | 1.62 | 3 | 103.7 | 0.05 |
| 5.2 | 1.8 | 1.58 | 1 | 103.4 | 0.02 |
| 5.6 | −0.9 | 1.59 | −1 | 104.8 | −0.01 |
| 6.0 | −2.5 | 1.60 | −2 | 106.6 | −0.02 |
| 6.4 | −2.9 | 1.63 | −2 | 108.4 | −0.03 |

In the 2 mm layer adjacent to the bottom surface, the flow has a strong inward secondary flow relative to the primary flow, as the two velocity ratios show in the table. The upward component of velocity is relatively much smaller than the radially inward and angular component of velocity. Therefore, the embryos once inside the boundary layer will be effectively swept to the centre in a matter of few seconds. If we substantially increase the rate of rotation, the radial velocity and the ratios vary favourably, however, the boundary layer thickness will also decrease substantially, as shown in Table 4. Here, only the rate of rotation has increased from 15 rpm to 120 rpm.

TABLE 4

Radial, axial and angular components of the fluid velocity and the ratio of the radial to axial and radial to angular velocity inside the boundary layer from the bottom wall at z = 0 to 2.3 mm for the rate of rotation ζ = 120 rpm at radial position r = 7 mm.

| z (mm) | $v_r$ (mm/s) | $v_z$ (mm/s) | $\frac{v_r}{v_z}$ | $v_\theta$ (mm/s) | $\frac{v_r}{v_\theta}$ |
|---|---|---|---|---|---|
| 0.0 | 0.0 | 0.00 | | 0.0 | |
| 0.1 | −306.7 | 0.69 | −445 | 337.3 | −0.91 |
| 0.3 | −421.2 | 2.21 | −190 | 646.9 | −0.65 |
| 0.4 | −395.5 | 3.90 | −101 | 891.4 | −0.44 |
| 0.6 | −289.1 | 5.32 | −54 | 1048.9 | −0.28 |
| 0.7 | −155.0 | 6.19 | −25 | 1119.0 | −0.14 |
| 0.8 | −31.8 | 6.56 | −5 | 1118.4 | −0.03 |
| 1.0 | 58.3 | 6.49 | 9 | 1071.6 | 0.05 |
| 1.1 | 107.9 | 6.84 | 16 | 1003.9 | 0.11 |
| 1.3 | 120.6 | 5.67 | 21 | 935.9 | 0.13 |
| 1.4 | 106.4 | 5.21 | 20 | 881.1 | 0.12 |
| 1.6 | 77.2 | 4.83 | 16 | 845.4 | 0.09 |
| 1.7 | 44.0 | 4.59 | 10 | 829.2 | 0.05 |
| 1.8 | 14.3 | 4.47 | 3 | 827.5 | 0.02 |
| 2.0 | −7.4 | 4.50 | −2 | 838.3 | −0.01 |
| 2.1 | −19.6 | 4.52 | −4 | 852.6 | −0.02 |
| 2.3 | −23.6 | 4.61 | −5 | 867.1 | −0.03 |

The velocity of the inward secondary flow has increased substantially forcing the embryos to reach the centre of the boundary layer more rapidly. However, the boundary layer thickness now is only 2.3 mm, and the region with the effective secondary stream is limited to about 0.8 mm above the plate for the 120 rpm case compared to 2.4 mm in the 15 rpm case.

The two examples above show that based on the size of the embryos and for specific separator container (5) dimensions, the rate of rotation can be used as a control parameter to adjust the boundary layer thickness and optimize the efficiency in separating and transferring the embryos into the axial region of the bottom wall (6).

Sink Vortex Considerations

A sink vortex can be generated in the separator container (5) by draining fluid through the conduit (7) when the area of the conduit (7) at the axial region of the bottom wall (6) of the separator container (5) is much smaller than the area of bottom wall (6) of the separator container (5). An alternative means of creating a sink vortex is by extending a suction tube from the top to the centre of the bottom wall (6) the separator container (5). Without loss of generality, and for the sake of clarity in explanation, we shall limit our explanation to the case where the conduit (7) is a round perforation with a diameter much smaller than the diameter of the bottom wall (6), positioned at centre of the bottom wall (6). In this case, the flow leaving through the conduit (7) takes on a rotating secondary motion forming a free vortex flow. When the conduit (7) diameter is less than 10% of the diameter of the bottom wall (6), then the effect of the vertical boundary can be neglected and the sink vortex forms freely. The characteristics of the sink vortex are an abrupt depression in the free surface of the liquid (22), and formation of a sink boundary layer (20) at the bottom of the separator container (5) around the conduit (7).

Figure 8:
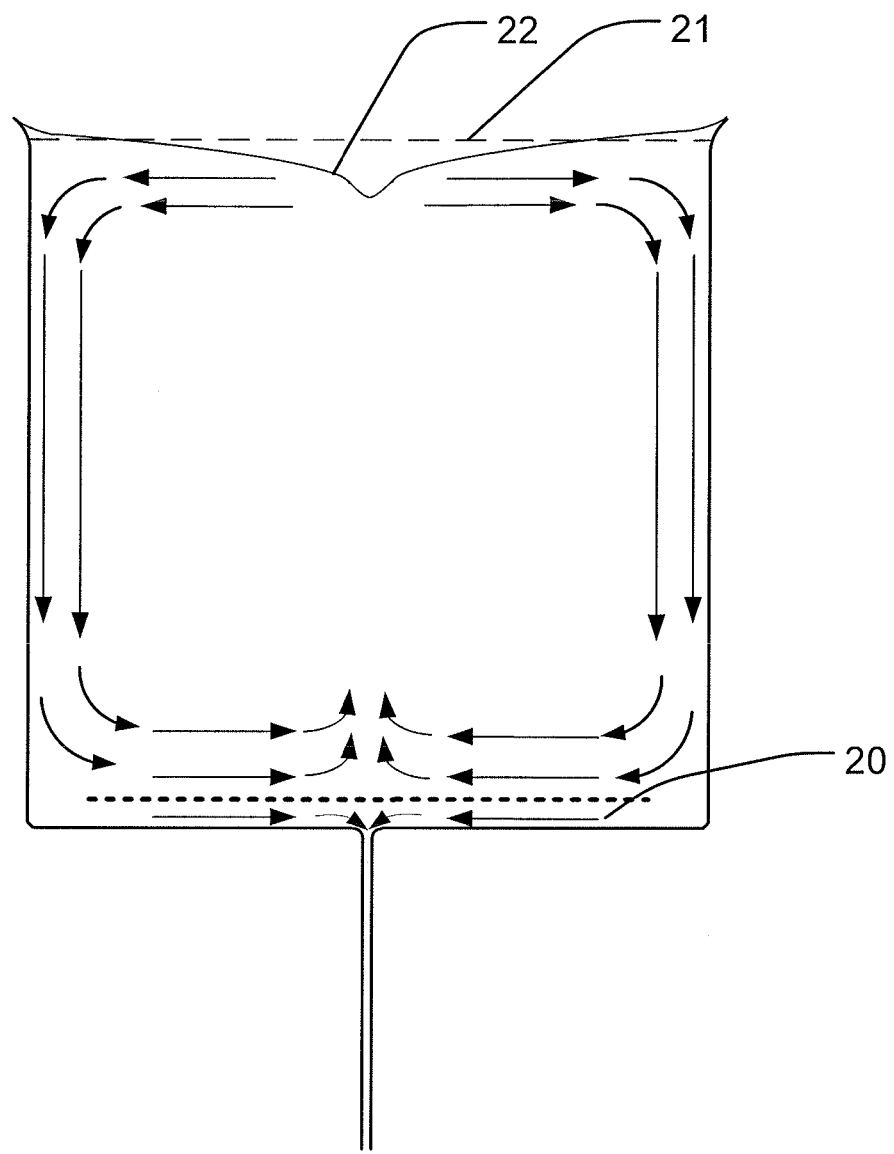
FIG. 8. Illustrates the secondary flow associated with the boundary layer during operation.
Figure 9:
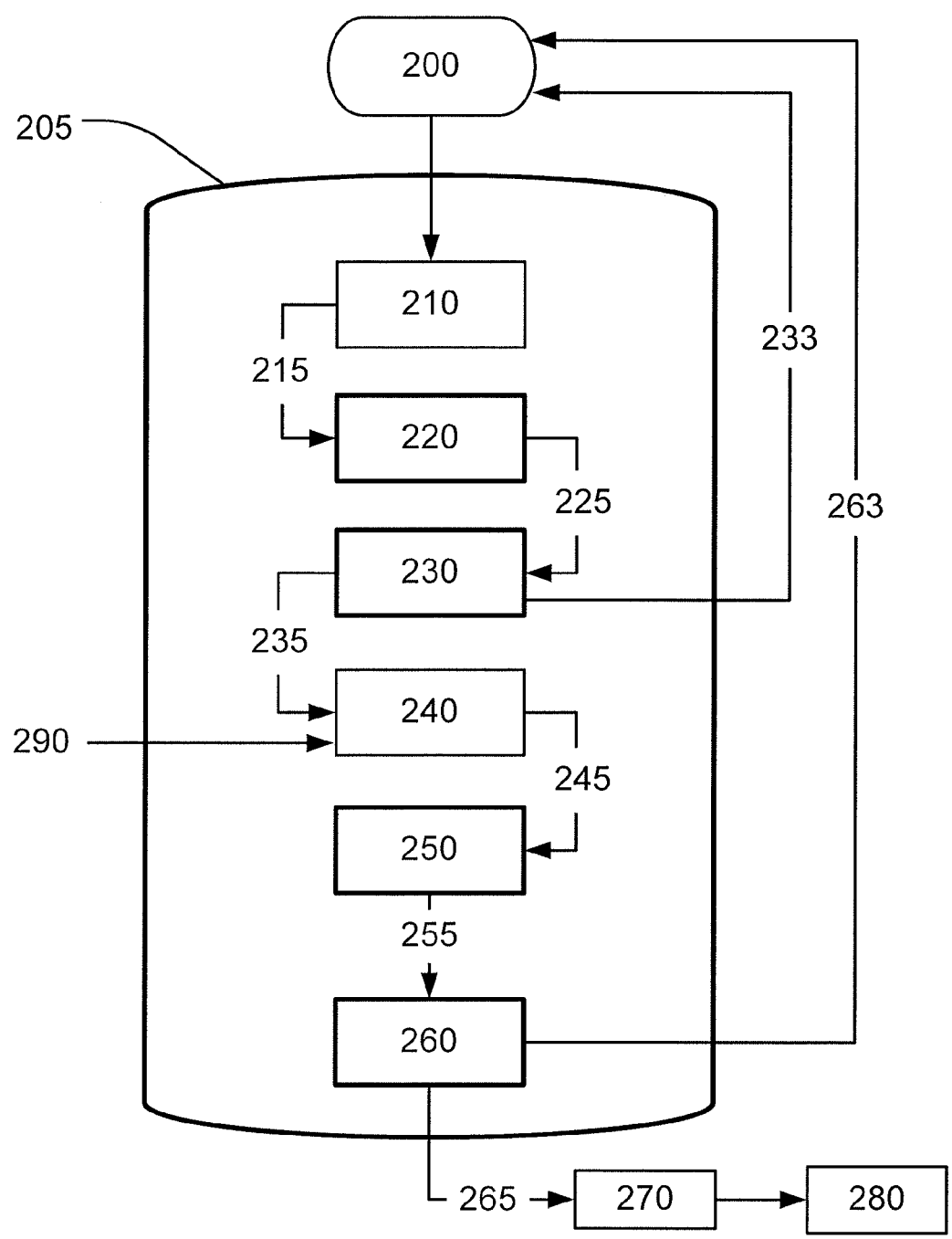
FIG. 9. Illustrates an embodiment of an automated system disclosing the units of operation.

The secondary flow associated with a sink vortex in the separator container (5) is illustrated in FIG. 8. Note the primary flow is the rotating flow around the central axis not shown in this figure. The portion of the secondary flow that remains outside the boundary layer does not enter the conduit (7) at the bottom wall (6). This can be illustrated by the following example: if we insert a long needle attached to a syringe in the flow, as long as the tip of the needle is outside the boundary layer, any dye injected by the needle will continue to rotate around the centre axis and some dye will follow the path of the secondary flow shown in FIG. 8. Only if the tip of the needle is held very close to the bottom surface will the dye enter the bottom hole with the draining fluid. Thus, only the fluid and any object that enters the boundary layer will enter the hole.

Since the dispersed embryogenic tissue has a large average drag because of the large surface to volume ratio, it will not enter the thin boundary layer as it quickly gets entrained back into the secondary flow outside of the boundary layer. However, the embryos will enter the boundary layer and follow the inward motion of the fluid into the conduit (7). It is this combination of the secondary motion of the fluid and the boundary layer that creates an easy and rapid way to separate the embryos from the embryogenic tissue into a separate stream of liquid leaving the separator container (5) through the conduit (7).

Separator Container (5)

The device of the invention comprises a separator container (5) that is fluid-filled during operation. Ideally, the separator container (5) is cylindrical in shape and has a flat bottom wall (6). Also ideally, the axis (10) of the cylinder is vertical, and the flat bottom is perpendicular to the axis. Although deviations from the ideal parameters result in less optimal operation, the device may nevertheless be operated with a certain level of deviations from the ideal geometry. The tolerances will vary from case to case.

Preferably, the separator container (5) is axially symmetric. Any deviations of axial symmetry will result in disturbances in the flow and consequently in lower efficiency of separation.

The angle of the flat bottom surface is also important for efficient separation of the embryos. A flat bottom wall (6) perpendicular to the axis (10 or z) of the separator container (5) is preferred.

If the bottom wall (6) angle is positive (upward), then the embryos have to travel axially upward (z increases) and radially inward (r decreases) through the boundary layer. This reduces the efficiency of separation because the embryo being heavier than the fluid tends to settle not to climb.

If the angle of the flat bottom surface is negative (downward), this will adversely impact the pressure gradient inside the boundary layer. That is the positive radial pressure gradient which is forcing the embryos inside the boundary layer towards the centre will reduce in magnitude exerting less inward force on the embryos. The angle at which the radial pressure gradient becomes so adversely impacted as to not have any impact on the embryos depends on the speed of rotation and the boundary layer characteristics. In general, assuming solid body rotation of the fluid with angular velocity in an open separator container (5), if the downward slope of the flat bottom surface at every point is such that, $$\frac{dz}{dr} = \frac{r\varsigma^2}{g}$$

where g is gravity, then the pressure gradient along the bottom surface will be very small everywhere on the surface except near the conduit (7) in cases where the sink vortex exists. This case will be a very inefficient geometry for embryo separation. If the slope is even larger, that is the bottom wall (6) is at a higher negative angle downward, then there will be an adverse pressure gradient along the surface.

The separator container (5) comprises a fluid conduit (7) located at the axial region of the bottom wall (6). Preferably, the fluid conduit (7) comprises a perforation of the bottom wall (6) located at the axis region (preferably the centre) of the separator container (5). The conduit (7) may also comprise a tube extended from the top of the separator container (5) to the axial region, preferably the center, of the bottom wall (6). The conduit (7) may also comprise a tube extended to the axial region, preferably the center, of the bottom wall (6) from any other direction.

The ratio of the conduit (7) area to the container bottom wall (6) area is important. The conduit (7) area should be relatively small (preferably less than 10% of the bottom wall (6) area).

The container may optionally comprise a second fluid outlet (25) near the top of the separator container (5). The second outlet (25) may be implemented by the separator container (5) not having a top wall whereby excess fluid may leave the separator container (5) though overflow.

The separator container (5) may also optionally comprise a third fluid outlet (16) at the bottom of the separator container (5) for draining fluid out of the separator container (5).

Dimensions of the separator container (5) may vary in specific embodiments, and as discussed above, the rate of rotation in the fluid may be used as a conveniently adjustable control parameter not requiring physical modifications to the device.

Means of Inducing Axisymmetric Rotating Flow in the Separator Container (5)

The terms means of inducing axisymmetric rotating flow in the separator container (5), rotation means or rotating device are used interchangeably throughout this disclosure.

The rotation means (18) may be a rotating object positioned inside the container, rotating in the liquid. The object may be connected to a motor (12) though a shaft (11). The object may also be induced to rotate by application of magnetic fields from the outside of the separator container (5).

When a solid object that is immersed in the liquid medium is rotating, the fluid particles immediately adjacent to the solid surface of the object stick to the surface (referred to as no-slip in fluid mechanics) and rotate with the surface. The fluid particles at the surface exert a frictional force (more accurately, shear stress) on the adjacent fluid particles which in turn propagate further away from the surface and into the fluid body. The said fluid shear stress in turn forces a rotating motion on the entire fluid inside the separator container (5). Given sufficient time, the motion of the fluid takes on a substantially solid body rotation, except near the outer solid boundaries and bottom wall (6) of the separator container (5) and the vicinity of the central axis (10), as discussed above.

Preferably, the rotating object exerts its effect on the fluid mainly though shear stress as described above, which results in minimal additional vortices beyond the desired ones. Thus, said rotating object is preferably disk- (18b) or cylinder-shaped (18a).

Another preferred implementation of rotation means (18) is to rotate the fluid inside the separator container (5) by rotating the entire separator container (5) relative to the bottom wall (6). The only difference is that the in this case, there is no boundary layer on the vertical surface of the separator container (5) boundary. However, a boundary layer with substantially same characteristics will exist at the bottom wall (6).

The desired rate of rotation for the fluid (relative to the bottom wall (6) to be achieved is determined as discussed above, and using the teachings above, a rotation means (18) can be constructed and operated by the skilled person in a manner to achieve the desired rate of rotation.

Means of Draining Fluid from the Axial Region of the Bottom Wall (6) During Operation The device may comprise means of draining fluid through the fluid conduit (7) at the bottom wall (6) of the separator container (5). The means of draining fluid may simply comprise providing the fluid in the separator container (5) an opportunity to flow though the conduit (7) by gravity, but may also be implemented using a pump. Preferably the means is controllable, e.g. by being equipped with a valve (36) or by using a controllable pump. By draining is herein meant any manner of extraction of fluid though the conduit (7) from the separator container (5), be it gravity-driven or driven by a pressure gradient, a pump or other means.

Means of Collecting the Separated Embryos

Means of collecting the separated embryos may comprise that the conduit (7) is placed and dimensioned such that embryos drawn into the axial region of the bottom wall (6) during operation enter into the conduit (7) by gravitational sedimentation. Preferably, the above means of collecting embryos further comprise means of collecting the embryos from the conduit (7) without substantially altering the volume of fluid in the container. Such means have the advantage of eliminating the sink vortex in applications where maximal purity is desired. Examples of above collecting means include a rotating gate valve arranged such that the embryos may sediment into the valve as well as out from the valve upon rotating the valve gate. Provided that all conduits around the gate valve are fluid-filled, no net flow results from collecting the embryos.

Another example comprises a first and a second valve arranged such that i) when the first valve is open and the second is closed the embryos may sediment into the conduit (7) towards the second valve;

ii) when the first valve is closed and the second is open, the embryos may sediment further into the conduit (7) beyond the second valve.

Such arrangement also allows collection of embryos from the conduit (7) without any volumetric flow.

Figure 7:
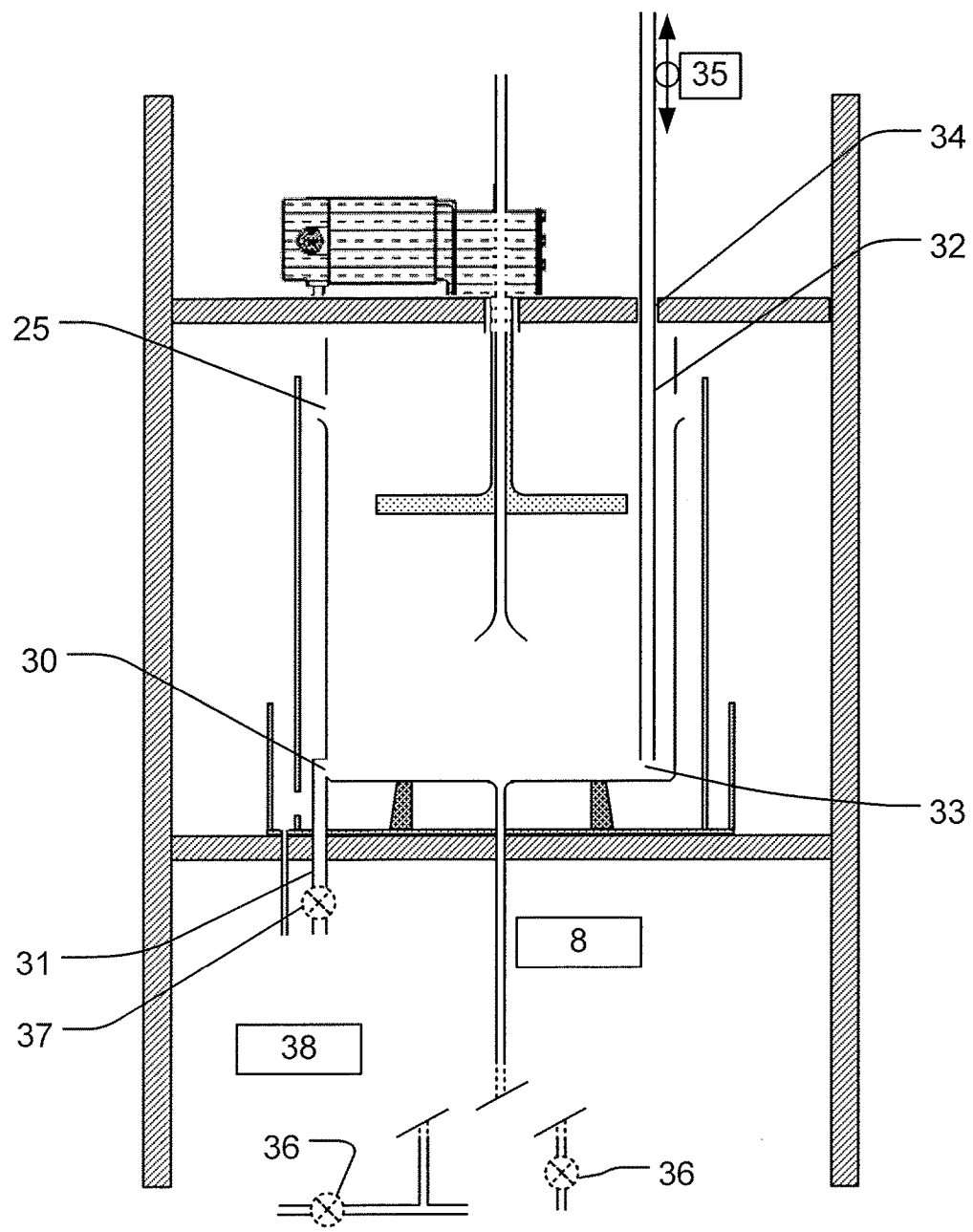
FIG. 7. Illustrates an embodiment of a separator device of the invention adapted for continuous use. A and B illustrate alternative means to regulate the flow through the conduit (7).

A further preferred exemplary means of collecting embryos comprises providing a tube intersection (having at least first, second and third connections) to the conduit (7), arranged as specified below (see FIG. 7A for an illustration of an exemplary embodiment).

The third connection comprises an outlet for fluid.

The conduit (7) is attached to the second connection. The intersection comprises a bottom surface, arranged such that embryos sedimenting in the conduit (7) will preferentially sediment on the bottom surface through the second connection.

Further, the means of collecting embryos comprises means of providing fluid flow from the first connection of the intersection, such that the embryos sedimented in the intersection bottom surface are swept into the third connection, from which they can readily be collected in the outflowing fluid.

The means of providing fluid flow preferably provides (during operation) adjusted fluid flow such that the pressure of the fluid flow provides a fluid pressure in the intersection counteracting the pressure in the conduit (7). Preferably, the fluid flow is adjusted such that there is zero or essentially zero net flow in the conduit (7). In some cases it may be preferable the fluid flow is adjusted such that there is net flow in the conduit (7) in the direction of the separator container (5). In such cases however, the net flow in the conduit (7) should not be so large as to induce such upward drag on the sedimenting embryos that the sedimentation stops.

Having net flow in the conduit (7) towards the separator container (5) has the advantage it is possible to that any immature embryogenic mass that might have entered in the conduit (7) may be blown back into the separator container (5). Recall that the immature embryogenic mass is exhibits larger drag and its sedimentation is therefore more easily counteracted than the sedimentation of the embryos.

On the other hand it may be preferable to adjust the fluid flow from the first connection such that a net flow from the separator container (5) takes place in the conduit (7), if it is desired to speed up the separation processing at the cost of purity.

The skilled person will appreciate that adjusting the fluid flow to provide suitable flow in the conduit (7) may be implemented in a large number of equivalent ways. Parameters that can be adjusted include the fluid column height in the conduit (7) and separator container (5), flow rate from the first connection, and flow rate through the third connection.

Means of collecting the separated embryos may also be implemented by drawing fluid though the conduit (7) and collecting fluid flowing out of the conduit (7). Alternatively, suction from a separate optional fluid outlet may be used to draw and collect the embryos from the axial region of the bottom wall (6). In embodiments where operation includes drawing fluid though the conduit (7) it is preferable that the means of collecting the separated embryos comprises means of selectively collecting a fraction of the fluid exiting the conduit (7). Such fraction collection means may be manually controlled or automatically controlled e.g. simply by timing.

The collection means may also comprise a sensor (8) which detects the presence or absence of an embryo in fluid exiting though the conduit (7). The sensor (8) may comprise a photo sensor. Photo sensors for use with the invention may be in principle any of the many photo sensors known in the art suitable for the purpose. Examples of suitable sensors include but are not limited to those based on one or more optical beam(s) including laser beam(s), induction sensors, sonic sensors including ultrasonic sensors. Input from the sensor (8) may be used to direct the fraction collection means to selectively collect a fraction of the outflowing fluid containing a predetermined concentration of embryos.

Means of Introducing the Fluid-Suspended Embryos and Immature Embryogenic Tissue into the Separator Container (5)

The fluid-suspended embryos and immature embryogenic tissue may be introduced into the separator container (5) either intermittently (batchwise) or continuously. The particulars of each manner of operating are disclosed separately below.

The means of introduction is preferably a feed conduit (9) suitable for delivering the fluid-suspended embryos and tissue, preferably to the axial region of the separator container (5), and preferably close to the surface of the fluid. The site of introduction is not very crucial, as long as the introduction site is located at least some distance away from the bottom wall (6) to allow sufficient distance for the embryos to separate from the tissue. The introduction means may be integrated into a shaft of the rotation means (18); e.g. a hollow shaft (11) may be used as a feed conduit (9) to introduce the embryos and tissue.

Separator Device and Methods Adapted for Batch Operation

In many cases, the embryogenic clusters being processed have to be fed into a dispersion stage batchwise from Petri dish or a bioreactor. For a separator device located downstream of the disperser unit this will result in uneven inflow of embryos. In this case, the liquid medium carrying the dispersed embryo and immature embryogenic tissue will be rich in embryos for a short period of time (referred to as "Rich" period) and then depleted in embryos for a time period. During the period between the separation of one batch of embryos and before introduction of the subsequent batch (e.g. during exchanges of the source for the embryogenic clusters being processed), there will be very few or no embryos present in the separator container (5) (referred to as "Depleted" period). Because it is beneficial to minimize the amount of immature embryogenic tissue inside the separator container (5), during the Depleted period the fluid medium in the separator container may preferably be replaced. Thus, a device of the invention adapted for batch operation preferably comprises means of replacing the fluid in the separator container (5).

The device may optionally comprise a sensor (8) monitoring the fluid exiting the embryo collection means. The sensor (8) may be used to monitor the transport of the embryos and to detect the occurrence of a depleted stream. Once the sensor (8) does not detect embryos for a designated period of time, it may signal the start of the Depleted period which causes the means of replacing the fluid in the separator container (5) to perform a fluid replacement operation.

The triggering of a fluid replacement operation may also be done manually or by timing the fluid replacement to occur a predetermined time period after the introduction of the latest batch of embryos.

The fluid replacement operation may be performed in several ways. The examples below should not be construed as limiting in any way, and features of found in the different examples may be freely combined.

For instance, pure medium may be injected in the separator container (5) though the means of introducing the fluid-suspended embryos. An optional valve (36) may be used to block any flow through the conduit (7) at the bottom wall (6), whereby the fluid will overflow though the second outlet (25), thus rapidly replacing the contents of the container with pure medium.

Alternatively, the device may optionally comprise a third outlet (30) at the extreme bottom of the separator container (5) equipped with a second valve (37), optionally operationally coupled to the first valve (36) at the conduit (7) at the bottom wall (6). During the fluid replacement operation, the second valve (37) will open and, optionally, the first valve (36) will close simultaneously allowing the fluid to exit from the third outlet (30) thus depleting the separator container (5) the fluid medium containing of immature embryogenic tissue material.

In yet another alternative, the means of replacing the fluid comprise an extraction tube (32) attached to a vertically oriented linear actuator (35) which be lowered to extract the liquid containing the immature embryogenic tissue from the separator container (5) to extract the fluid. Once the liquid is completely extracted, the extraction tube may be raised with the outlet (33) above the liquid level.

Alternatively, the fluid in the separator container (5) may also be drained though the conduit (7).

Once the liquid with immature embryogenic tissue is sufficiently drained, fresh fluid medium will be provided into the separator container (5) for the next batch of embryogenic mass to be processed.

Separator Device and Method Adapted for Continuous Operation

If the source of the embryogenic clusters being processed is continuous, the method and device of this invention can be used in a continuous operational mode for embryo separation. The device of the invention adapted for continuous operation preferably comprises means of continuously replacing the fluid in the separator container (5).

Preferably the means of continuously replacing the fluid in the separator container (5) comprise means of providing a flow rate of fresh medium to the separator container (5) (e.g. through the feed conduit (9)), that is much larger than the flow rate from the conduit (7), with excess flow containing the immature embryogenic tissue leaving the separator container (5), e.g. through the second outlet (25) and/or through a third outlet (30).

The factor by which the inward flow rate is greater than the outward flow rate though the conduit (7) can be decided depending on the level of desired separation efficiency. Higher relative inward flow rate will result in greater purification factor. In principle, the amount of remaining contaminating tissue mixed in the separated embryos will be inversely related to the factor by which the inward flow rate is greater than the outward flow rate though the conduit (7).

It is preferable that the inward flow rate exceeds the outward flow rate though the conduit (7) by a factor of about 3, 5, 10, 15, 20 or more. It may also be preferable that the inward flow rate exceeds the outward flow rate by a factor in the range of 1.1-1000, 2-100, 2-50, 2-20, 3-20, 5-15, 5-10, or 8-12. In certain embodiments, it is preferred that the outward flow rate through the conduit (7) equals zero or is substantially zero.

In the case of continuous operation mode, it is preferable that the embryos are continuously collected from the separator container (5) from the conduit (7). Other continuous means of collecting the embryos are also possible.

Control Unit

The control unit (38) has computational and storage capabilities, and can be provided as one physical unit, or alternatively as a plurality of logically interconnected units. The control unit (38) may be implemented in many ways. For instance, the control unit (38) could be an ordinary commercially available personal computer or a specifically tailored microprocessor-controlled control unit.

Means of controlling other units and receiving input from other units can be implemented in many ways, wired and wireless. For instance, the control unit may comprise a D/A converter input-output unit capable of producing analogue electric signals that can be transmitted through wires. The signals sent by the control unit (38) could be digital such as via serial port, parallel port, USB port, Firewire (IEEE1394) or similar wired signals. Alternatively, the signals could be wireless though acoustic, optical, infrared or radiofrequency signals. For example, the Bluetooth or wireless LAN technologies could be used to transmit the signals from the control unit (38) to the components to be controlled.

It should be noted that the control unit (38) comprises logic for performing the functionality of the separation device. This functionality may be implemented by means of a software or computer program. The control unit (38) may also comprise storage means or a memory unit for storing the computer program and processing means or a processing unit, such as a microprocessor, for executing the computer program. The storage means may also be readable storage medium separated from, but connected to the control unit (38). When, in the above, it is described that the separator device or the deposition device performs a certain function it is to be understood that the control unit (38) in the separator device or the deposition device uses the processing means to execute a certain part of the program which is stored in the storage means.

Separator with Two or More Containers

Two or more separator devices as described above can be connected in series to achieve higher purity of embryos. For instance, a first separator device with high outward flow rate through the conduit (7) (resulting in high speed but low purity) may be used upstream, and the output of the first separator device may be directly fed into a second separator device with slower operation but higher purification factor. Alternatively, a slower separation device with higher purification factor could be used as the upstream device and a faster one downstream. Combinations of more than two separator devices are also possible and may be preferred for applications where purity is of utmost importance.

Method for Separating Somatic Embryos from Embryogenic Tissue

The invention also relates to a method of segregating and separating fluid-suspended embryos from immature embryogenic tissue. The method entails the use of a suitable fluid-filled container, preferably a separator container (5) as described above.

The method is based on utilizing a combination of effects that in concert effectively and rapidly cause segregation and separation of embryos from the immature embryogenic tissue. The method comprises the following:

a) inducing a forced axisymmetric rotating flow in the separator container (5), described above, relative to the bottom wall (6) and optionally (b) creating a sink vortex at the bottom of the separator container (5) by draining the fluid from the conduit (7) at or near the centre of the bottom wall (6).

The forced rotating flow is such that a thin boundary layer is formed at the bottom wall. In cases involving the use of the optional sink vortex, there is an additional boundary layer (sink boundary layer) forming near the draining conduit (7) due to the sink vortex. The method also comprises having a positive pressure gradient in the separator container (5). Said pressure gradient is created by the rotating fluid. The method comprises the utilization of the characteristics of a boundary layer so formed beneath a rotating fluid, optionally in combination of a sink vortex, as elaborated herein. The rotating fluid creates a positive pressure gradient with substantially equal magnitude inside and outside the boundary layer. Outside the boundary layer, the objects rotate with the flow approaching an equilibrium orbit where the inward force due to the positive pressure gradient balances the centrifugal force due to the rotation of the object. This balance between the centrifugal force and the force due to pressure gradient does not exist inside the boundary layer, since the rate of rotation of the objects decreases substantially inside the boundary layer. The method is additionally based on a key difference in the hydrodynamic feature of the embryo with respect to the immature embryogenic tissue. The drag force on an embryo is substantially less than the drag force on immature embryogenic tissue due to the large difference in the surface to volume ratio. Due to this difference, the embryos settle and easily enter the boundary layer; however, the immature embryogenic tissue also settles but does not enter the boundary layer. Instead, the immature embryogenic tissue continues to remain entrained in the primary rotating fluid. The embryo inside the boundary layer is initially pushed toward the centre axis by the dominating force due to the positive pressure gradient. When approaching the centre, the embryo may be quickly trapped inside the sink vortex (if present) and may easily be collected therefrom. Alternatively, the embryos are simply collected from the axial region of the bottom wall (6).

The method thus comprises segregating the embryos from the embryogenic tissue at the boundary layer (20) and optionally also separating the embryos into a liquid stream free of immature embryogenic tissue by the presence of the sink vortex.

Preferably, the conduit (7) outward (from the separator container (5)) flow rate is zero or essentially zero, and the embryos enter the conduit (7) by gravitational settlement. Inducing an inward flow in the conduit (7) may be preferable as it may further improve purity by pushing away embryogenic mass from the conduit (7). However, the upward drag force on the embryo due to the inward liquid velocity in conduit (7) should not exceed the weight of the embryo minus the weight of the displaced liquid by the embryo (buoyancy effect); otherwise, the embryo will move inward in conduit (7).

Method Adapted for Batch Operation

The method may be adapted for batchwise operation, in which case it further comprises collecting the embryos by selectively collecting embryos from the axial region of the bottom wall (6) during a time period after introduction and after the sedimentation of the embryos has occurred, but before the immature embryogenic tissue has had time to sediment. Preferably, the batchwise method also comprises the step of replacing the fluid medium in the separator container (5) prior to introduction of the subsequent batch.

Method Adapted for Continuous Operation

The method may be adapted for continuous operation, in which case it further comprises using a separator container (5) with a second outlet (25) at the top of the separator container (5), feeding fluid into the separator container (5) at a rate exceeding the rate fluid flow from the conduit (7). Preferably, the embryos are collected from the conduit, preferably in the fluid exiting the conduit (7).

3. Orientation and Sorting Unit

Detailed description of the method and device for detecting, sorting and orienting means for deposition of mature embryos in the correct orientation in an appropriate substrate disclosed in patent application PCT/US09/39982 is hereby incorporated by reference in its entirety.

The orientation and sorting unit disclosed in PCT/US09/39982 is useful as a stand-alone method or in combination with the disperser and separator means in the automated system of the present invention. PCT/US09/39982 provides an apparatus for detection and automated orientation of plant embryos such as somatic plant embryos. An apparatus having additional capability of sorting acceptable embryos from other objects is also provided.

Apparatus of PCT/US09/39982 for automatic orienting of plant embryos suspended in a liquid flowing though the apparatus comprises:

a) flow channels for the liquid comprising liquid inlet (501) of an inlet tube (502), liquid outlet (503) of an outlet tube (504), reservoir tube (505) connected to a reservoir device (506), said reservoir device comprising means for generating positive liquid pressure in relation to the liquid pressure at outlet (503), means for accommodating liquid flowing in as well as means of providing liquid for outward flow, wherein the inlet tube (502), the outlet tube (504) and the reservoir tube (505) are connected at an intersection (507), and wherein the flow channels are dimensioned such that embryos may travel with the liquid flowing though the channels but are restricted to travelling either in a crown-first or crown-last orientation by dimensional constraints without a possibility to change orientation while travelling through any of the said tubes unless the change in orientation occurs as disclosed further below;

b) flow direction means (518) comprising means of:
  i) directing the flow from the inlet (501) to the outlet (503);
  ii) directing the flow from the inlet (501) to the reservoir device (506); and
  iii) directing the flow from the reservoir device (506) to the outlet (503);

c) detector(s) comprising an orientation detector (510) placed in the inlet tube (502), wherein the orientation detector (510) comprises means of determining the orientation of an embryo passing though the inlet tube (502);

d) control unit (38) for steering the flow of the liquid in the flow channels comprising means of receiving input from the orientation detector (510) and means controlling the flow direction means (518) such that:
  i) in a default position, when no embryo is detected by the orientation detector (510), the flow direction means (518) is controlled such that the flow of the liquid in the flow channels is directed from the inlet (501) to the outlet (503);
  ii) when an embryo having an orientation matching a predetermined orientation is detected by the orientation detector (510), the flow direction means (518) is controlled such that the flow of the liquid in the flow channels is directed from the inlet (501) to the outlet (503);
  iii) when an embryo having an orientation opposite to the predetermined orientation is detected by the orientation detector (510), the flow direction means (518) is controlled such that the flow of the liquid in the flow channels is directed from the inlet (501) toward the reservoir device (506) so that the embryo enters the reservoir tube (505), after which the flow direction means (518) is controlled such that the flow of the liquid in the flow channels is directed from the reservoir device (506) to the outlet (503) so that the embryo enters the outlet tube (504), after which the flow direction means (518) is controlled such that the flow of the liquid in the flow channels is directed from the inlet (501) to the outlet (503);

whereby all embryos suspended in the liquid exiting from the outlet (503) will have an orientation matching the predetermined orientation.

Apparatus additionally capable of sorting acceptable embryos from other objects is also disclosed in PCT/US09/39982 comprising:

a) flow direction means (518) additionally comprise means of directing the flow into either an embryo receiver (340) or a secondary destination (521);

b) the orientation detector (510) additionally comprises means of separating acceptable embryo from other objects;

c) control unit (38) comprises additional means of controlling the flow direction means (518) such that:
  i) in a default position, when no object is detected by the orientation detector (510), the flow direction means (518) is controlled such that the flow of the liquid in the flow channels is directed from the inlet (501) to the outlet (503) and the outlet flow is directed into the secondary destination (521);
ii) when an object other than an acceptable embryo is detected by the orientation detector (510), the flow direction means (518) is controlled such that the flow of the liquid in the flow channels is directed from the inlet (501) to the outlet (503) and the outlet flow is directed into the secondary destination (521);
iii) when an acceptable embryo having an orientation matching a predetermined orientation is detected by the orientation detector (510), the flow direction means (518) is controlled such that the flow of the liquid in the flow channels is directed from the inlet (501) to the outlet (503) and the outlet flow is directed into the embryo receiver (340);
iv) when an acceptable embryo having an orientation opposite to the predetermined orientation is detected by the orientation detector (510), the flow direction means (518) is controlled such that the flow of the liquid in the flow channels is directed from the inlet (501) to the reservoir device (506) so that the embryo enters the reservoir tube (505), after which the flow direction means (518) is controlled such that the flow of the liquid in the flow channels is directed from the reservoir device (506) to the outlet (503) so that the embryo enters the outlet tube (504), after which the flow direction means (518) is controlled such that the flow of the liquid in the flow channels is directed from the inlet (501) to the outlet (503) and the outlet flow is directed into the embryo receiver (340);

whereby all acceptable embryos suspended in the liquid exiting from the outlet (3) will be directed into the embryo receiver (340) and will have an orientation matching the predetermined orientation and whereby other objects are sorted into the secondary destination (521).

The apparatus of PCT/US09/39982 may more specifically be characterised by that:
a) the flow direction means comprise an inlet valve (508) placed in the inlet tube (502) and outlet valve (509) placed in the outlet tube (504), wherein said valves provide means of controlling the flow in the flow channels by opening and closing in response to control signals;
b) the control unit (38) comprises means of controlling the valves (508) and (509) such that:
i) in a default position, when no embryo is detected by the orientation detector (510), the inlet valve (508) is open and the outlet valve (509) is open, whereby the flow of the liquid in the flow channels is directed from inlet (501) to outlet (503);
ii) when an embryo having an orientation matching a predetermined orientation is detected by the orientation detector (510), the inlet valve (508) remains open and the outlet valve (509) remains open, whereby the flow of the liquid in the flow channels remains directed from inlet (501) to outlet (503); and
iii) when an embryo having an orientation opposite to the predetermined orientation is detected by the orientation detector (510), the inlet valve (508) remains open and the outlet valve (509) is closed, whereby the flow of the liquid in the flow channels is directed from inlet (501) to the reservoir device (506) so that the embryo enters the reservoir tube (505), after which the inlet valve (508) is closed and the outlet valve (509) is opened whereby the flow of the liquid in the flow channels is directed from the reservoir (506) to outlet (503) so that the embryo to enters the outlet tube (504), after which the inlet valve (508) is opened and the outlet valve (509) remains open, whereby the flow of the liquid in the flow channels is again directed from inlet (501) to outlet (503) as in the default position;

whereby all embryos suspended in the liquid exiting from the outlet (503) will have an orientation matching the predetermined orientation.

The apparatus of PCT/US09/39982 may more specifically comprise one or more of the following:
(a) an additional reservoir tube detector (511) comprising means of detecting the presence or absence of an embryo in reservoir tube (505), in which case the control unit (38) comprises means of receiving input from the reservoir tube detector (311) to determine when an embryo has entered the reservoir tube (505) by waiting for the reservoir tube detector (511) to detect the presence and the location of an embryo in the reservoir tube (505); and/or
(b) an additional outlet tube detector (12) comprising means of detecting the presence or absence of an embryo in the outlet tube (504), in which case the control unit (38) comprises means of receiving input from the outlet tube detector (512) to determine when an embryo has entered the outlet tube (504) by waiting for the outlet tube detector (512) to detect the presence and location of an embryo in the outlet tube (504); and/or One or more cases when an object or an embryo is to enter a particular location may be determined by a predetermined timing based on a constant flow rate of the liquid flowing though the apparatus of PCT/US09/39982.

The reservoir device (506) may comprise a liquid container open to atmospheric pressure containing liquid having a surface level higher relative to the outlet (503) such that the hydrostatic pressure is sufficient to provide liquid flow in the flow channels from the reservoir device (506) to outlet (503) when the flow direction means are set accordingly.

The reservoir device (506) may preferably have a much larger horizontal cross-sectional area compared to the cross-sectional area of the reservoir tube (505), such that the level of liquid inside reservoir (506) is substantially constant during operation.

The valves (508) and/or (509) may be solenoid pinch valves.

The orientation detector (510) preferably comprises a digital imaging means and computerized image analysis means.

The orientation and sorting unit disclosed in PCT/US09/39982 provides at least the following advantages:
 Planting the embryo in the correct orientation
 Low cost
 Accurate orienting, and facilitating sorting of viable embryos from other objects
 Imaging and characterization of each somatic embryo is made possible
 Fast processing of large numbers of embryos
 Gentle handling of somatic embryos in liquid phase increases conversion rate of mature embryos to germinated embryos
 Efficient apparatus allows for sufficient yield of mature embryos also from cell lines that are only producing limited numbers of mature embryos 4. Deposition for Germination Method of Depositing Embryos for Germination by a Free Jet The deposition method of the present invention is based on delivering an embryo, processed in any manner prior to such delivery, to an embryo receiver (340) by means of a free jet of fluid. The method has the advantage of not requiring any moving mechanical parts such as conveyer belts or robotic arms.

A method of depositing a plant somatic embryo in an embryo receiver (340) is disclosed, comprising the steps of:
i) providing a fluid-suspended plant embryo in a desired orientation;
ii) providing a suitable embryo receiver;
iii) optionally, providing means to stabilize the free jet of fluid carrying the embryo
iv) introducing the plant embryo into the embryo receiver (340) using means of a free jet of fluid while maintaining the desired orientation.

The means to stabilize the free jet of fluid carrying the embryo may be used to counteract any liquid jet instability that may occur, as shown to occur in some cases as discussed below The method may preferably further comprise using means of generating a free jet of fluid having a flow channel (387) with an essentially linear straight section immediately upstream of the outlet of the means. The straight section (370) has a length of at least one inside diameter (380) of the flow channel, but preferably 10 times the inside diameter of the flow channel.

Device for Depositing Embryos

The embryo delivery device and the embryo receiver are capable of transporting and holding the embryo, respectively, while preserving the orientation of the embryo. Although the preferred fluid medium carrying the embryo here is liquid, more preferably water, other liquid or gaseous fluids such as air are also within the scope of this invention.

The device of the invention comprises means of forming a free jet (360) of fluid emanating from the outlet (365) of a flow channel, wherein the free jet is aligned with an embryo receiver (340) with features outlined further below.

The flow channel section immediately upstream of the point of outlet (365) has an essentially linear straight section (370) with length at least equal to one largest inside cross-sectional dimension (380), but preferably 10 times the largest inside cross-sectional dimension of the flow channel. The straight section of the flow channel (370) immediately upstream of the outlet (365) allows for the jet of fluid leaving the outlet to be substantially unidirectional with substantially parallel streamlines without secondary streams.

Figure 12:
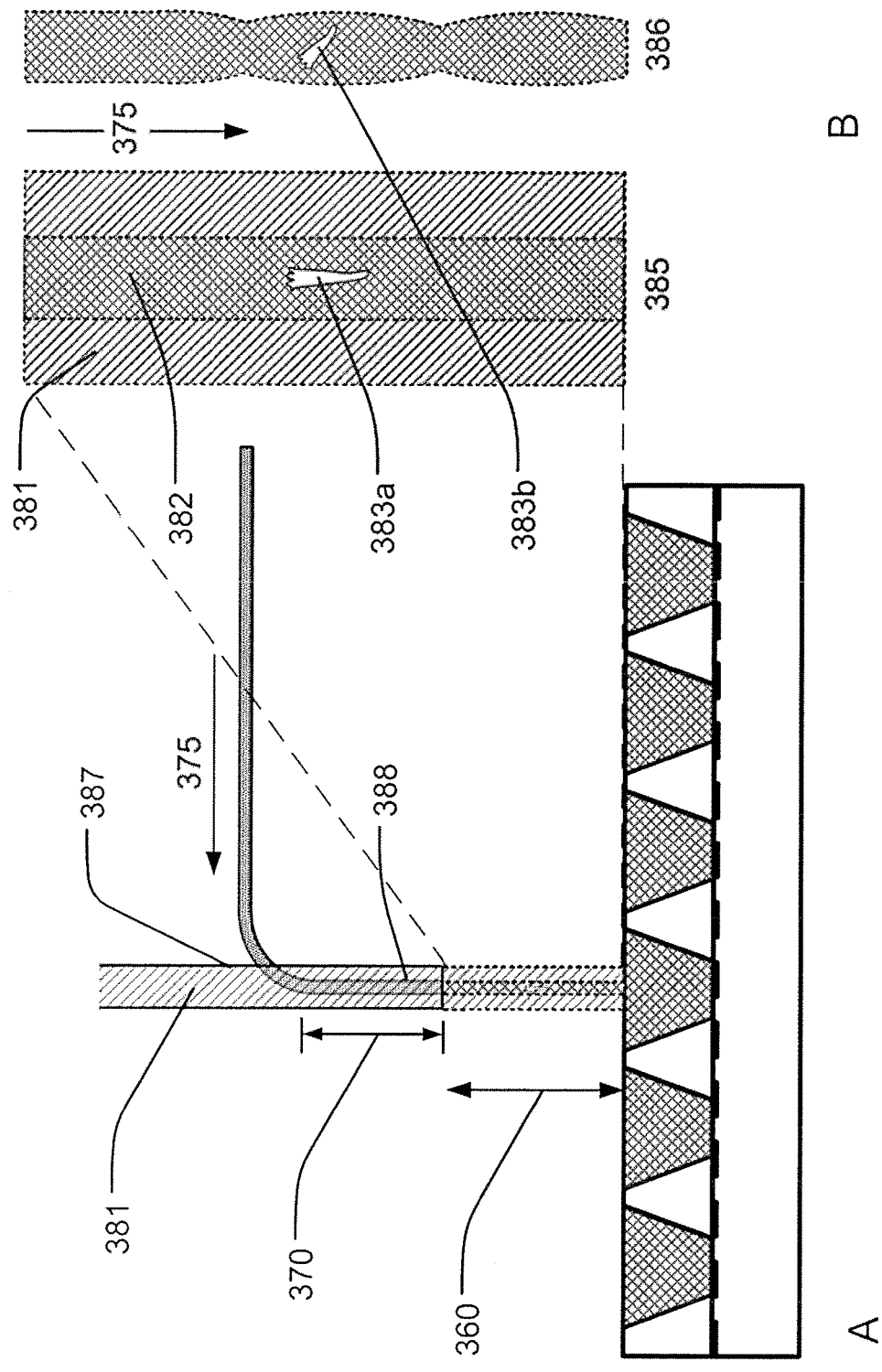
FIG. 12. Illustrates the deposition of oriented embryos.

Without limiting the variations in design, it is preferred that the outlet tip of the nozzle (365) to be at least one largest inside cross-sectional dimension and preferable about three largest inside cross-sectional dimensions above the inlet or the top surface of the embryo receiver. In other words, the free jet (360) leaving the outlet (365) has a preferable length that is one to three times the largest inside cross-sectional dimension. When the outlet (365) tip is closer than one tube largest inside cross-sectional dimension to the inlet of the embryo receiver, the liquid overflow may disturb the jet and the embryo delivery. When the tip is further than three tube largest inside cross-sectional dimensions away from the receiver, it is more difficult to keep the jet stable and precisely aligned with the receiver, and the embryo may have enough time to rotate and slightly change orientation (386) causing problems when entering the receiver, as illustrated in FIG. 12.

In the case of liquid jets, which are preferred in this invention, depending on the length of the free jet and the mean velocity of the free jet, the surface tension of the liquid and the radius of the liquid jet, the free jet may become unstable and form a corrugated shape (386) which could lead to jet breakup. This phenomena, known in the field of hydrodynamic instability as Rayleigh instability (see Hydrodynamic Instability by Drazin and Reed; ISBN 0 521 28980 7, 1987), results in free liquid jet breakup given enough time. For example, in a preferred embodiment of the embryo deposition device, where the largest inside cross-sectional dimension is about 4.2 mm (that is, the diagonal of a 3×3 mm square cross-section of the channel), the preferred length of the free jet is about 12.5 mm and the hydraulic diameter of the round jet is about 3.4 mm. It can be shown based on linear stability analysis that the corrugated form of the disturbance leading to such instability and jet breakup will grow by an exponential factor e, that is by a factor of about 2.7 times, in 2 ms. For a jet speed of about 0.5 m/s, the growth of the disturbance by a factor of 2.7 will occur in about 1 mm length of the free jet. Therefore, the jet after 10 mm could start to show large disturbances. The means to stabilize the jet disclosed herein as part of the deposition device (260), is based on the knowledge of hydrodynamic instability and the parameters that are included in the growth of the primary destabilizing mode in the free jet.

The reason for the instability of a free liquid jet is the effect of the liquid surface tension and the liquid jet curvature. A slight disturbance causing an axisymmetric deformation of the jet slightly decreases the radius of curvature of the jet increasing the effect of surface tension which in turn further forces the radius to decrease magnifying the effect of the disturbance forcing the jet into a corrugated shape which eventually breaks up the jet. This phenomena is clearly visible with the free jet leaving a nozzle. As flow rate decreases, the instability and the liquid breakup comes closer and closer to the tube outlet (365). For cases where it is necessary to have a slow free liquid jet delivering the embryo into the receiver, this instability becomes large enough to cause the embryo to rotate inside the free liquid jet (386), and not be deposited properly inside the embryo receiver container (340).

The primary mode of instability grows exponentially as $e^{st}$ where $s=0.34(r^3\rho/\sigma)^{-0.5}$, and here in this growth rate equation, r, $\rho$ and $\sigma$ are respectively the radius, density and surface tension of the liquid jet. If this instability prevails, the free liquid jet delivery system of this invention will not be reliable in terms of consistently delivering the embryo into the container and preserving the orientation of the embryo.

For slow liquid delivery jets, the jet may be stabilized by essentially removing the free surface of the delivery jet (381), that is the interface between the liquid and air, by encapsulating the jet (382) inside another liquid jet with larger diameter (381). This in effect removes the air surrounding the delivery jet (that is the jet containing the embryo) and in effect replaces a smaller diameter jet with a larger diameter jet. Since as shown by the growth rate equation above, the rate of growth of the disturbance depends on radius of the jet to the power of −3/2; when radius increases from 4.2 mm to 8.4 mm, the rate of growth of the instability decreases by about a factor of 3. This results in a substantially more stable delivery jet. Since the instabilities first appear on the free-surface of the jet, in the encapsulated delivery jet, the outer liquid layer becomes unstable first leaving the inner delivery jet substantially stable long enough for slow delivery jets to remain substantially stable and straight preserving the orientation of the embryo at the point of delivery to the container of the embryo receiver.

In many situations when the embryo and the embryo delivery jet have to move much slower (that is much less than 0.5 m/s), a typical free liquid jet 12 mm or longer with about 3 mm diameter will be unstable and the delivery operation may fail to preserve the orientation of the embryo being deposited into the container of the embryo receiver. A much unstable jet with corrugated shape (386) may not even remain straight enough to deliver the embryo inside the container. An optional means to stabilize the jet in this situation is to encapsulate the delivery jet (382) with an outer fluid jet (381) by placing the delivery tube (388) inside an outer tube (387) with a sealed joint. By adjusting the flow rate in the outer tube (387), the inner delivery jet (381) will be substantially more stable and therefore provides a more reliable means of depositing the embryo to the embryo receiver in a manner to preserve the orientation of the embryo (383a).

Although different liquids can be used as the inner and outer fluids, it is preferred to use the same liquid for the inner and outer fluid in order to eliminate an interface between the delivery jet (383) and the encapsulating jet (381). When using the same liquid, no interfacial tension exists between the delivery and the encapsulating jets.

Without limitations, it is preferred to match the mean velocity of the delivery and encapsulating jets such that the fluids in each jet travel substantially with the same velocity. It should be noted that any viscous fluid moving adjacent to a stationary solid surface will have a zero velocity at the solid surface, the no-slip principle in fluid dynamics. Therefore, the liquid immediately adjacent to the inner and outer solid surfaces of the inner tube (388) will have a zero velocity. At the tube outlet (365), the velocity at the interface between the delivery jet and the encapsulating jet increases from zero right at the outlet toward reaching the mean free jet velocity. In order to avoid creating extra shear in between the delivery and the encapsulating jets, it is preferred to adjust the flow rate of the encapsulating jet in order to have the same mean velocity in the encapsulating jet as in the delivery jet. In practice, this can be achieved by calculating the mean velocity in the encapsulating jet based on the flow rate and the cross-sectional area of the encapsulating jet (381).

Thus, the deposition device may optionally comprise means increasing the stability of the delivery jet comprising means of encapsulating the delivery jet delivering the embryos in another jet with a substantially larger diameter.

Embryo Receiver

An embryo receiver of the invention can be a container or any growing chamber for receiving an embryo, such as an artificial seed or a germination container, as long as the embryo receiver (340) is constructed such as to receive and hold the embryo while preserving the orientation of the embryo.

In the construction of an embryo receiver (340), the physical dimensions of the receiver, the properties of the substrate as well as sufficient draining capacity (when using liquid to deposit the embryos) are important.

The dimensions of the receiver must be large enough to accommodate the embryo and small enough to preserve the desired orientation. The embryo receiver also must have an initial opening diameter at least equal to the largest cross-sectional diameter of the embryo, but preferably at least 10% larger to allow the embryo to enter with the free jet. The receiver for use with liquid jet carrier requires means of draining excess carrier liquid that enters the receiver together with the embryo. Preferably, the receiver is perforated (345) to achieve the drainage. Preferably, at least one of the perforations (345) is located at the bottom of the receiver to most fully drain excess fluid from the container. Preferably, the embryo receiver has a cylindrical or conical shape. A conical-shaped receiver with the inlet diameter at least two times larger than the largest cross-sectional diameter of the embryo, and with a flat perforated bottom with a radius of at most the smallest diameter of the embryo and an axial length of at least two times the length of an embryo would be one of the preferred shapes of the container. Such shape of the container is preferred because it allows the excess liquid to pass and drain freely while the embryo is being deposited first unconstrained from the inlet side of the container and then more restrained when reaching the bottom of the container; such that preserving the orientation and keeping the embryo in a substantially vertical orientation.

The substrate (320) needs to be sufficiently rigid as to keep the embryo in the desired orientation, yet flexible enough to allow development.

The fluid travelling through a flow channel (350) without the embryo has a volumetric fluid flow rate equal to the average speed of the fluid multiplied by the cross-sectional area of the tube. In one embodiment, the tube is made of glass with 3 mm by 3 mm square cross-section at the inside. The average speed of the liquid is 50 cm/s. Therefore, the volumetric flow rate is 4.5 ml/s. With the embryo suspended in liquid through the tube, the embryo is substantially sliding over a lubricating thin film of liquid adjacent to the glass wall allowing easy and smooth translation of the embryo with reduced drag on the embryo as opposed to the embryo being in dry contact with the glass wall. There is always a small amount of drag on the embryo, and therefore, the embryo moves slightly slower than the average velocity of the fluid inside the flow channel. If the inside diameter of the flow channel does not change along the flow stream, then the velocity of the embryo will remain substantially constant, and it is simple to accurately predict the timing for delivering each successive embryo into the designated embryo receiver by means of a fluid stream being forced through a flow channel by a substantially constant pressure head or pressure gradient. Therefore, it is preferred that the shape and the cross-sectional area of the delivery tube remain substantially constant. In case of liquid, the constant pressure head can be provided by keeping a reservoir of fluid at an appropriate height to get a constant pressure head sufficient to move the stream of liquid and the embryos through the tube with substantially constant and steady velocity. In one setup, a tube with a 3×3 mm square cross-section and two ninety degree bends required 0.12 m of liquid head to move the embryos at the speed of about 0.5 m/s through a 1.2 m section of the tube. Although it is preferred to deliver the embryo vertically in the direction of gravity into the embryo receiver, it is also possible and at times may be advantageous to force the fluid free jet and embryo to enter an embryo receiver in a direction other than vertical and downward. A jet of fluid leaving a nozzle at 0.5 m/s remains substantially straight and substantially stable for a distance of 10 mm or more as it leaves the tube outlet (365). Therefore, it is feasible to deposit the embryo in a direction other than vertical-downward into an embryo receiver (340).

5. System

Without loss of generality, we use somatic embryogenesis as an example of production from in vitro cultured plant propagules. Somatic embryogenesis technology for mass propagation of plants has been limited because of the requirement for tedious manual operations. The methods to make plants from somatic embryos require intensive manual handling, and are therefore expensive for plant production. The underlying reason for this is the tedious and time-consuming laboratory procedure for manually selecting, separating, sorting, orienting and planting of the embryos during maturation, germination, and plant formation processes. It is an object of this invention to provide the method and devices for an automated system capable of selecting and depositing mature embryos that satisfy a set of defined criteria to germinate and form plants in with minimal human interference. With this automated system, the processes of selecting and separating the mature embryos from the cluster of embryos produced in petri dish or in a liquid bioreactor, sorting, orienting and depositing the embryos for germination can be completed in a matter of seconds.

Each unit of the invention disclosed herein or by reference may be used as a stand-alone unit but is preferably an integrated part of a larger system for automation of mass propagation of large-scale production of in vitro cultured plant propagules.

The system of the invention comprises one or more of the following components:
  a) disperser unit (220) to disperse the embryos and the embryogenic tissue suspended in a fluid (located upstream of the separator device) and optionally also a bioreactor, as embryo source, located upstream of the disperser,
  b) separator device, (230) located downstream of the disperser unit, to effectively separate the mature embryos into a stream of liquid medium without most of the immature embryogenic tissue.
  c) sorting and orienting unit, (250) located downstream of the separator device for imaging and sorting the embryos according to set criteria and identifying the orientation of the embryos for deposition further downstream.
  d) deposition device, (260) located downstream of the sorting and orienting unit, for deposition of the selected and oriented mature embryos into an embryo receiver (340) for germination and root formation.

The separator unit of the invention may be used as a stand-alone unit or preferably combined and integrated with the disperser unit disclosed in PCT/US09/39982 as a disperser-separator system for rapid extraction of the mature embryos from the embryogenic cluster produced in a petri dish on solid medium or from a bioreactor with liquid medium. In this case, the outlet of the last disperser tube is attached to the feed conduit (9) of the separator, as illustrated in FIG. 10. The embryogenic clusters dispersed in the disperser (220) are immediately guided into the separator container (5) through the feed conduit (9) of the separator while the fluid in the separator container is rotating by the rotation means (18). The embryos dispersed with the embryogenic mass in the separator container settle more rapidly and enter the boundary layer (20) at the bottom plate (6) of the separator container. Upon entrance in the boundary layer, the embryos rapidly follow a converging spiral path to the centre of the bottom plate (6) and enter the conduit (7). This combination of the disperser and separator units in a sub-system provides the means to rapidly and effectively separate embryos from the embryogenic clusters produced in petri dish on solid medium or in bioreactors in liquid medium into a stream of liquid containing only embryos. As illustrated in FIG. 12, the said stream of liquid with only embryos can be combined with other units, as disclosed herein, to image and analyse the characteristics of the embryos and the orientation of the embryos for either deposition in a suitable plate for germination or reject the embryos that do not meet the set criteria for acceptable embryos.

The criteria for acceptable embryos depend on the type of embryos being processes.

As an example, for Norway spruce, the criteria includes but are not limited to having embryos with clear cotyledon, elongated tale and total length that is at least two times larger than the average diameter of the embryo's cross-sectional plane. The shape must be relatively straight and not too curved.

To evaluate each embryo against the set criteria for production of plants in a fast and cost-effective manner, the embryos separated into a liquid stream with only embryos leaving the conduit (7) of the separator unit (230) will be immediately guided into the orientation and sorting unit (250), with a liquid conduit guiding individual embryos through a test section (249), as shown in FIG. 12. In the test section, the embryo is detected by optical sensors and imaging systems. The image of the embryo is examined based on image analysis. The characteristics of the embryo are then tested against a set of criteria for "acceptable" embryos which would most likely germinate and form plants with further processing. If the embryo passing through the test section is not acceptable, that is it does not satisfy the set criteria, and is rejected. The embryo orientation is also determined and changed is not correct.

Figure 11:
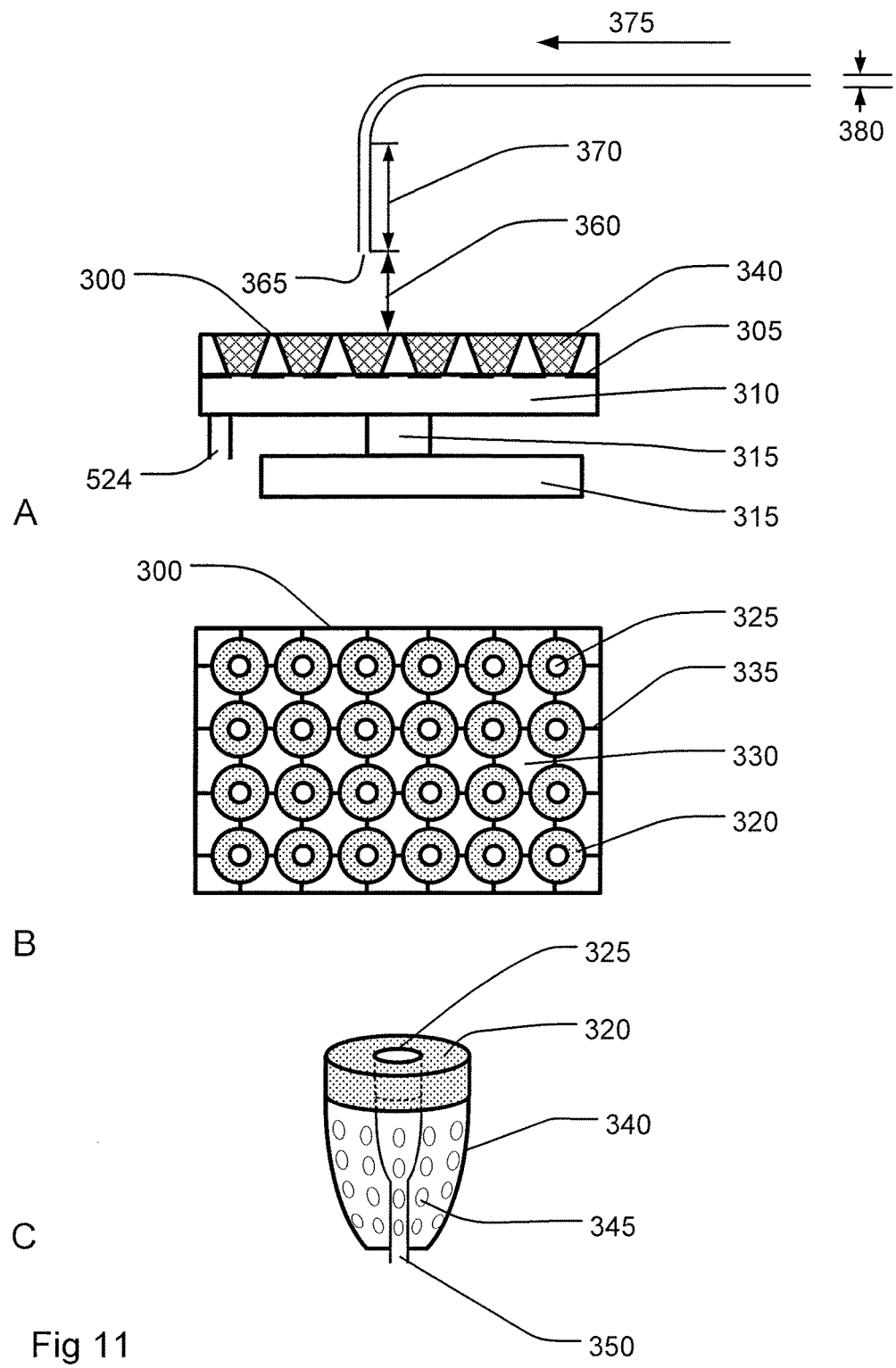
FIG. 11. Illustration of the deposition for germination and the germination unit.

The correctly oriented and acceptable embryos are passed on in a liquid conduit to the deposition device (260) and deposited in embryo receivers (340). In one embodiment, an XY table will position a singularreactor plate such that the next empty embryo receiver container in this plate is directly and precisely under the outlet nozzle (365) deposition device long enough for the acceptable embryo to be deposited into the container. As soon as the embryo leaves the outlet of the deposition device and is deposited in the container of the singularreactor plate, the XY table will position the singulareactor plate such that the liquid leaving the exit nozzle (365) will be deposited outside of the embryo receiving containers (300) and into the reject section (310), as shown in FIG. 11. Also, rejected embryos are directed outside of the embryo receiving containers.

Each time an acceptable embryo is detected and deposited, the computer software may record the image of the embryo, the sequential number, the position in the plate where the embryo has been deposited, the date and time of deposit, and a unique code for the embryo. Once the embryo receiver is full, it may be transported manually and installed in the respective docking station for germination and root formation.

System without Orientation Module

During tests of the system with the orientation module (250) it was noted that the orienting step could be rate-limiting in relation to deposition. The when the embryo had to be re-oriented the placement into the embryo container (340) took about four times longer than the embryo deposition time for an embryo with correct initial orientation.

Figure 16:
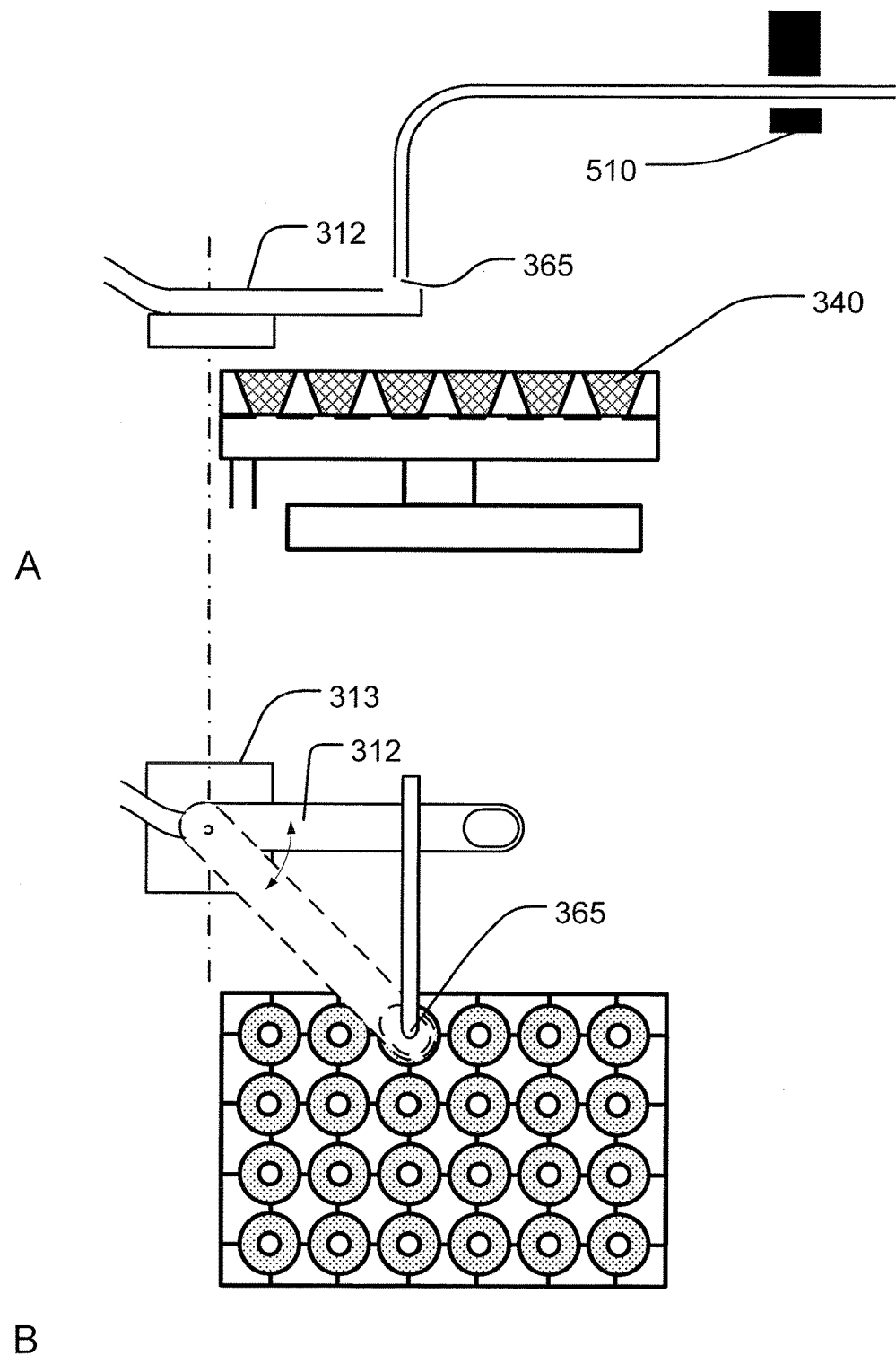
FIGS. 16A-B. Illustrates a side (FIG. 16A) and top (FIG. 16B) view of an embryo collector.

In order to speed up the system the orientation module (250) was removed and instead an alternative type embryo collector (312) was constructed. The embryo collector (312) is shown in FIG. 16 (A side view, B top view). The embryo collector is controlled by step motor/switch (313) and the controlling unit (38) in such a way that when an embryo is indentified with the orientation detector (510) located upstream the outlet (365) the step motor/switch (313) can position the embryo collector (312) according to the orientation of a passing embryo.

The orientation detector (510) and the controlling unit (38) may for example be an imaging system interfaced with a computer identifies the orientation of the passing embryo. If the identified embryo has the tail/root first it will let the embryo pass to the embryo container (340), if the embryo has the head first, the step motor/switch (313) will position the embryo collector (312) such that the embryo is collected. After collection the embryo is returned back to the system, either to the separator (230) or to the dilutor (240). With this set up the system performed well and the speed of correctly deposited embryos was increased by a factor of two compared to a system with orientation module (250).

The examples below should be construed as non-limiting.

EXAMPLES

Example 1

Separation

Several clusters of embryogenic mass of Norway Spruce (cell line 06:28:05) with average hydraulic diameter of the cross-section taken from the mid-section of the cluster ranging from 5 mm to 30 mm were collected from a periodically and partially immersed bioreactor and fed into a disperser☐ of the PCT/US09/39981. An in vitro culture container as disclosed in WO9625484 was used as the bioreactor Upon passage through the disperser, the embryos fully dispersed in water, were fed through the feed conduit (9) and into the separator container (5). The rotation means (a disk) was rotating at the rate of 120 rpm for more than 20 minutes with the separator container (5) full of water prior to the injection of the clusters of embryogenic mass into the disperser. It is preferred to have the rotation means running for more than few minutes to eliminate the initial transients due to starting of the motor with a stationary liquid. A 500 mm glass flask was placed under the conduit (7) to collect the material leaving the separator container (5). A plastic tube attached to the conduit (7) glass tube was attached to another glass tube (glass tube 1) inserted through the rubber cork pressure-fitted on the top of the flask and extended to about 5 mm from the bottom of the flask. Another glass tube (glass tube 2) was pressure-fitted through the rubber cork of the flask extending all the way to the middle height of the flask. A plastic tube was attached to the top of the glass tube 2 and guided into a reservoir placed at an elevation much below the bottom of the flask.

Initially the plastic tube connecting the conduit (7) tube to the top of glass tube 1 was pinched shut so no flow could go through the conduit (7) tube. Shortly prior to the injection of the dispersed embryos in the separator container (5), the said tube initially pinched was opened so liquid could flow through the conduit (7) glass tube as dictated by the pressure head in the separator container (5). It was observed that the flow rate of the liquid through the conduit (7) was initially higher (as expected) until the liquid level in the flask reached the bottom tip (inlet) of the glass tube 2. A valve downstream of the conduit (7) (at the top) of the glass tube 2 was adjusted to keep the liquid level stationary inside the flask. Upon injection of the cluster of the embryogenic mass in the disperser, the fully dispersed embryogenic mass leaving the disperser entered the separator container (5) rapidly being entrained in the flow. In about 3 minutes, the plastic tube connecting the conduit (7) tube to glass tube 1 was pinched shut, and the motor and the flow was stopped. Also the valve downstream of glass tube 2 was closed. Since the bottom of tube 2 is about 50 mm above the bottom of the flask, and the embryos in the flask settle to the bottom of the flask, only liquid from the top portion of the flask is removed by glass tube 2 due to the pressure head difference in the flask. The liquid and suspended material inside the separator container (5), the flask and the reservoir downstream of the flask were collected and inspected carefully. Of the total of 52 embryos collected in the entire system, 45 were in the flask and 8 in the separator container (5) and none in the reservoir downstream of the glass tube 2. Repetition of the experiments with this system provided similar results with the ratio of recovered embryos being about 60 to 85%.

The rotating means (18) in the system of this example was made with stereolithography and attached to a hollow shaft of the motor. It was observed that the rotating means was slightly 'wobbling', that is not being precisely axi-symmetric, creating a rather periodic travelling wave at the liquid surface. The other reason for this slight deviation from the ideal axi-symmetric flow is the imprecision in the diameter and circular shape of the glass separator container (5) used in the experiments. In general, if the separator container (5) and the rotating means (18) and the entire system is machined precisely to create an ideal axi-symmetric flow, the efficiency in collecting the embryos is expected to increase.

Example 2

Deposition

The deposition device of the invention, as shown in FIG. 11, comprises an x/y table with linear actuators (315) and a Singulareactor plate with 20 or more containers, each container for one individual embryo. The linear actuators (315) are attached to a control unit (38).

The embryo receiver is fixed on top of the x/y table in a precisely known position, such that the linear actuator software can accurately position the plate. The embryo receiver plate comprises a plurality of containers, preferably 50 or more, in a grid formation, preferable rectangular grid formation, with a specific centre-to-centre spacing, preferably about 25 mm.

The container can have any shape appropriate for the application, preferably conical shape with a flat bottom, as shown in FIG. 11A. The wall and bottom of the container are perforated (305) to allow liquid medium to enter and drain freely into and out of the container. The embryo receiver plate contains a reservoir section (310) with an inlet (330) and an outlet (524), as shown in FIG. 11B. The entire system with the XY table are placed inside a hood to keep the entire system sterile. The embryo receiver plate can also be equipped with an airtight cover to be able to transfer under sterile condition.

Example 3

Separation with Two Separation Units

In order to get pure and well separated mature embryos two separator (230) units were connected in series. The outlet tube (7) from the first separation unit was connected to the feed conduit (9) on the second separation unit. With this set up the amount of immature embryogenic tissue was reduced by 95% or more.

Example 4

Separation with No or Minute Sink Vortex

There is a clear relation between the rate of liquid drainage through conduit (7) and the purity of the embryos being separated. By "purity" in this context is meant the effectiveness of separation of the immature embryogenic tissue from the embryos; higher purity means less embryogenic mass per embryo. The slower the rate of liquid drainage through the conduit (7), the slower the rate of separation and the more effective is the separation process in terms of purity.

Based on these observations, a device was made which has almost zero liquid flow rate from conduit (7) and let the embryos settle down through this outlet and continuously collect the embryos.

In this mode, the rate of embryo settlement is based on the number density of the embryos inside the separator container and the rate of rotation of the fluid. In one experiment it was shown that when about 75 to 100 embryos inside the container, the rate of embryo separation (almost zero flow rate through the outlet) is in the order of 1 embryo per second at rotation rate of 150 rpm.

Example 5

A disperser, as presented in FIGS. 13 and 14 and in the description above was connected to a separator as shown in Example 1. The starting material was cuttings or leaves from poplar (Populus trichocarpa) which was grown for a few weeks to develop calluses. These calluses was further grown to develop plantlets. Calluses and plantlets was picked and was injected into the disperser and the separator. The plantlets was finally recovered after the separation with no traces of callus tissue.

Further Aspects of the Invention

Aspect 1. A method of separating fluid-suspended embryos from immature embryogenic tissue comprising the steps of:

a) providing a suitable separator container (5), said container containing fluid having a density lower than of the embryos to be separated, being essentially cylindrical in shape, having an essentially flat bottom wall (6) and an essentially vertical axis;
b) inducing an axisymmetric rotating flow in the fluid relative to the bottom wall (6), thus:
i) creating a viscous boundary layer (20) at the bottom wall (6); and
ii) creating a radial pressure gradient in the separator container (5);
c) introducing the fluid-suspended embryos and immature embryogenic tissue to be separated into the fluid present in the separator container (5) at a location away from the bottom wall (6), thus:
i) sedimenting the embryos faster than the immature embryogenic tissue;
ii) allowing the embryos to enter the viscous boundary layer (20) while not allowing the immature embryogenic tissue to enter the viscous boundary layer (20);
iii) drawing the embryos entering the viscous boundary layer (20) into the axial region of the bottom wall (6); and
d) collecting embryos from said axial region of the bottom wall (6),
whereby the embryos collected are essentially separated from immature embryogenic tissue.

2. The method according to aspect 1, further comprising
a) providing a suitable separator container (5) further comprising a conduit (7) in communication with the fluid in the container at the axial region of the bottom wall (6) during operation;
b) creating a sink vortex at the axial region of the bottom wall (6) by draining fluid from said conduit (7); and
c) collecting embryos from said axial region of the bottom wall (6) in the fluid drained from the conduit (7).

3. The method according to aspect 1, further comprising
a) providing a suitable separator container (5) further comprising a conduit (7) in communication with the fluid in the container at the axial region of the bottom wall (6) during operation, wherein the conduit (7) is placed and dimensioned such that embryos drawn into the axial region of the bottom wall (6) during operation enter into the conduit (7) by gravitational settlement; and
b) collecting embryos from said conduit (7).

4. The method according to aspect 3, further comprising the step of modulating the sedimentation velocity of the embryos in the conduit (7) by means of inducing fluid flow through the conduit (7) into the separator container (5).

5. The method according to any of aspects 1-4, wherein the method is adapted for batchwise operation and further comprises selectively collecting the embryos during a time period after the sedimentation of the embryos has occurred but before the immature embryogenic tissue has had time to sediment.

6. The method according to any of aspects 1-5, wherein the method additionally comprises the step of replacing the fluid in the separator container (5) after processing a batch of embryos with fresh fluid.

7. The method according to any of aspects 1-4, wherein the method is adapted for continuous operation such that it comprises feeding fluid into the separator container (5) at a rate exceeding the rate of fluid flow from the conduit (7).

8. A further aspect is a device for separating fluid-suspended embryos and immature embryogenic tissue from each other comprising:

a) separator container (5), which during operation contains fluid having a density lower than the density of the embryos to be separated, said container being essentially cylindrical in shape, having an essentially flat bottom wall (6), an essentially vertical axis and comprising a fluid conduit (7) in communication with the inside of the container, located at the axial region of the bottom wall (6);
b) means of inducing an axisymmetric rotating flow in the fluid relative to the bottom wall (6), whereby during operation:
i) a viscous boundary layer (20) is created at the bottom wall (6);
ii) a radial pressure gradient is created in the separator container (5);
c) means of introducing the fluid-suspended embryos and immature embryogenic tissue to be separated into the fluid present in the separator container (5) at a location away from the bottom wall (6), whereby during operation:
i) the embryos sediment substantially faster than the immature embryogenic tissue;
ii) the embryos enter the viscous boundary layer (20) while the immature embryogenic tissue remains substantially outside the viscous boundary layer (20);
iii) the embryos entering the viscous boundary layer (20) are drawn into the axial region of the bottom wall (6) and into the conduit (7); and
d) means of collecting embryos from said conduit (7);
whereby the embryos collected are essentially separated from immature embryogenic tissue.

9. The device according to aspect 8, wherein
i) the conduit (7) is placed and dimensioned such that embryos drawn into the axial region of the bottom wall (6) during operation enter into the conduit (7) by gravitational sedimentation.

10. The device according to any of aspects 8-9, wherein the means collecting embryos comprise means of collecting the embryos from the conduit (7) without substantially altering the volume of fluid in the container.

11. The device according to aspect 10, wherein the means of removing the embryos from the conduit (7) without altering the volume of fluid in the container comprise a valve or a set of valves (36).

12. The device according to any of aspects 8-9, wherein
   i) the device comprises means of draining fluid from said conduit (7), whereby during operation a sink vortex is created at the axial region of the bottom wall (6); and
   ii) the means of collecting embryos comprise means of collecting the embryos from the sink vortex in the fluid drained from the conduit (7).

13. The device according to any of aspects 8-12, wherein the device is adapted for batchwise operation and further comprises means of collecting the embryos selectively during a time period after the sedimentation of the embryos has occurred but before the immature embryogenic tissue has had time to sediment.

14. The device according to any of aspects 8-12, wherein the device is adapted for continuous operation and further comprises a separator container (5) comprising a second outlet (25) at the top of the separator container (5) and means of feeding fluid into the separator container (5) at a rate exceeding the rate of fluid flow from the conduit (7).

15. The device according to aspect 14, wherein the second outlet (25) is implemented by means of a separator container (5) which is open at the top.

16. The device according to any of claims 14-15 wherein the means of collecting embryos from the sink vortex comprise means of collecting the fluid exiting the conduit (7).

17. The device according to any of aspects 8-16, wherein the device additionally comprises means of replacing the fluid in the separator container (5).

18. The device according to any of aspects 8-17, wherein the device comprises means of draining fluid from the axial region of bottom wall (6) during operation, comprising a conduit extended from above or any other direction to the proximity of the axial region of the bottom wall (6).

19. The device according to any of aspects 8-18, wherein the separator container (5) has a diameter in the range of 3-30 cm.

20. The device according to any of aspects 8-19, wherein the fluid conduit (7) has an area of 0.01%-10% of the area of the bottom wall (6).

21. The device according to any of aspects 8-20, wherein the means of inducing an axisymmetric rotating flow result in a rotational speed in the range of 5-1200 rpm in the fluid.

22. The device according to any of aspects 8-21, wherein the means of inducing an axisymmetric rotating flow comprise a rotating disk- or cylinder-shaped object.

23. The device according to any of aspects 8-22, wherein the means of introducing embryos and tissue is located at an axial location near the surface of the fluid.

24. The device according to any of aspects 8-23, wherein the fluid height during operation is 0.8-1.2 times the diameter of the separator container (5).

25. A further aspect is a method for depositing a fluid-suspended plant embryo in an embryo receiver while maintaining the orientation of the embryo comprising the steps of:
i) Providing a suitable embryo receiver (340) having means of draining fluid from the receiver;

ii) Providing a flow channel dimensioned such that the embryos may travel with the fluid flowing through the channels but are restricted to travelling either in a crown-first or crown-last orientation by dimensional constraints, said flow channel having an outlet (365) wherein said flow channel comprises a flow channel section immediately upstream of the outlet (365) having a straight section (370) with length at least equal to the largest cross-sectional inside dimension of the flow channel;

iii) Placing an embryo in the flow channel; and iv) Forming a free jet (360) of fluid emanating from the outlet (365), aligning said free jet with the embryo receiver (340) and depositing the embryo from the flow channel into the receiver (340) by using said free jet as a carrier means.

26. The method of aspect 25, further comprising the steps of:
   i) Determining the orientation of the embryo in the flow channel;
   ii) In case the orientation does not match the desired orientation, directing the embryo away from the embryo receiver (340); and
   iii) In case the orientation does match the desired orientation, directing the embryo into the embryo receiver (340).

27. A further aspect is a device for depositing fluid-suspended plant embryos while maintaining the orientation of the embryo comprising:
i) a flow channel dimensioned such that the embryos may travel with fluid flowing though the channel but are restricted to travelling either in a crown-first or crown-last orientation by dimensional constraints, said flow channel emanating to an outlet (365);
ii) an embryo receiver (340); and
iii) means of forming a free jet (370) of fluid emanating from the outlet, wherein the free jet during operation is aligned with an embryo receiver (340) thus allowing embryos suspended in the fluid to be deposited in the embryo receiver (340);
characterized in that
the means of forming a free jet comprise a flow channel (380) section immediately upstream of the outlet (365) having a straight section (370) with length at least equal to the largest cross-sectional inside dimension of the flow channel (380).

28. The device according to aspect 27, wherein the length of the straight section (370) is at least 10 times the largest cross-sectional inside dimension of the flow channel (380).

29. The device according to any of aspects 27-28, wherein outlet tip (365) is positioned during operation one to three flow channel diameters away from the embryo receiver (340).

30. The device according to any of aspects 27-29, wherein the embryo receiver (340) has an opening for depositing the embryo having a smallest dimension of at least 10% larger than the largest cross-sectional diameter of the embryo to be deposited.

31. The device according to any of aspects 27-30, wherein the device further comprises means stabilising the jet delivering the embryos comprising means of encapsulating the jet delivering the embryos in another fluid jet with substantially larger diameter.

The invention claimed is:
1. A method of separating fluid-suspended plant propagules from non-plant propagule tissues comprising the steps of:
   a. providing a suitable separator container, said container containing fluid having a density lower than of the embryos to be separated, being essentially cylindrical in shape, having an essentially flat bottom wall and an essentially vertical axis, and comprising a conduit in communication with the fluid in the container at an axial region of the bottom wall during operation, and providing a rotation object positioned inside the container for inducing an axisymmetric rotating flow;

b. creating a sink vortex at the axial region of the bottom wall by draining fluid from said conduit, and inducing an axisymmetric rotating flow in the fluid relative to the bottom wall by rotating the rotation object, thus:
  i. creating a viscous boundary layer at the bottom wall; and
  ii. creating a radial pressure gradient in the separator container;

c. introducing the fluid-suspended plant propagules and the non-plant propagule tissues to be separated into the fluid present in the separator container at a location away from the bottom wall, thus:
  i. sedimenting the plant propagules faster than the non-plant propagule tissues tissue;
  ii. allowing the plant propagules to enter the viscous boundary layer while not allowing the non-plant propagule tissues to enter the viscous boundary layer;
  iii. drawing the plant propagules entering the viscous boundary layer into the axial region of the bottom wall; and d. collecting plant propagules from said axial region of the bottom wall in the fluid drained from the conduit, whereby the collected are essentially separated from the non-plant propagule tissue.

2. The method according to claim 1, further comprising
a. providing a suitable separator container further comprising a conduit in communication with the fluid in the container at the axial region of the bottom wall during operation, wherein the conduit is placed and dimensioned such that plant propagules drawn into the axial region of the bottom wall during operation enter into the conduit by gravitational settlement; and
b. collecting plant propagules from said conduit.

3. The method according to claim 2, further comprising the step of modulating the sedimentation velocity of the plant propagules in the conduit by means of inducing fluid flow through the conduit into the separator container.

4. The method according to claim 1, wherein the method is adapted for batch wise operation and further comprises selectively collecting the plant propagules during a time period after the sedimentation of the plant propagules has occurred but before the non-plant propagule tissue has had time to sediment.

5. The method according to claim 1, wherein the method additionally comprises the step of replacing the fluid in the separator container after processing a batch of plant propagules with fresh fluid.

6. The method according to claim 1, wherein the method is adapted for continuous operation such that it comprises feeding fluid into the separator container at a rate exceeding the rate of fluid flow from the conduit.

7. A device for separating fluid-suspended plant propagules and non-plant propagule tissue from each other comprising:
a. separator container, which during operation contains fluid having a density lower than the density of the plant propagules to be separated, said container being essentially cylindrical in shape, having an essentially flat bottom wall, an essentially vertical axis and comprising a fluid conduit in communication with the inside of the container, located at the axial region of the bottom wall;
b. rotation object positioned inside the container for inducing an axisymmetric rotating flow in the fluid relative to the bottom wall, whereby during operation:
  i. a viscous boundary layer is created at the bottom wall;
  ii. a radial pressure gradient is created in the separator container;
c. means of introducing the fluid-suspended plant propagules and non-plant propagule tissue to be separated into the fluid present in the separator container at a location away from the bottom wall, whereby during operation:
  i. the plant propagules sediment substantially faster than the non-plant propagule tissue;
  ii. the plant propagules enter the viscous boundary layer while the non-plant propagule tissue remains substantially outside the viscous boundary layer;
  iii. the plant propagules entering the viscous boundary layer are drawn into the axial region of the bottom wall and into the conduit; and
d. means of collecting plant propagules from said conduit; whereby the plant propagules collected are essentially separated from non-plant propagule tissue.

8. The device according to claim 7, wherein
i. the conduit is placed and dimensioned such that plant propagules drawn into the axial region of the bottom wall during operation enter into the conduit by gravitational sedimentation.

9. The device according to claim 8, wherein the means collecting plant propagules comprise means of collecting the plant propagules from the conduit without substantially altering the volume of fluid in the container.

10. The device according to claim 9, wherein the means of removing the plant propagules from the conduit without altering the volume of fluid in the container comprise a valve or a set of valves.

11. The device according to claim 8, wherein
i. the device comprises means of draining fluid from said conduit, whereby during operation a sink vortex is created at the axial region of the bottom wall; and
ii. the means of collecting plant propagules comprise means of collecting the plant propagules from the sink vortex in the fluid drained from the conduit.

12. The device according to claim 8, wherein the device is adapted for batchwise operation and further comprises means of collecting the plant propagules selectively during a time period after the sedimentation of the plant propagules has occurred but before the non-plant propagule tissue has had time to sediment.

13. The device according to claim 8, wherein the device is adapted for continuous operation and further comprises a separator container comprising a second outlet at the top of the separator container and means of feeding fluid into the separator container at a rate exceeding the rate of fluid flow from the conduit.

14. The device according to claim 13, wherein the second outlet is implemented by means of a separator container which is open at the top.

15. The device according to claim 14, wherein the means of collecting plant propagules from the sink vortex comprise means of collecting the fluid exiting the conduit.

16. The device according to claim 8, wherein the device additionally comprises means of replacing the fluid in the separator container.

17. The device according to claim 8, wherein the device comprises means of draining fluid from the axial region of bottom wall during operation, comprising a conduit extended from above or any other direction to the proximity of the axial region of the bottom wall.

18. The device according to claim 8, wherein the separator container has a diameter in the range of 3-30 cm.

19. The device according to claim 8, wherein the fluid conduit has an area of 0.01%-10% of the area of the bottom wall.

20. The device according to claim 8, wherein the means of inducing an axisymmetric rotating flow result in a rotational speed in the range of 5-1200 rpm in the fluid.

21. The device according to claim 8, wherein the means of inducing an axisymmetric rotating flow comprise a rotating disk or cylinder-shaped object.

22. The device according to claim 8, wherein the means of introducing plant propagules and tissue is located at an axial location near the surface of the fluid.

23. The device according to claim 8, wherein the fluid height during operation is 0.8-1.2 times the diameter of the separator container.

24. A system for processing plant propagules suspended in a fluid, comprising a separator device according to claim 8, and one or more components selected from the group consisting of:
   a. disperser unit to disperse the plant propagules and the embryogenic tissue suspended in a fluid, located upstream of the separator device, and optionally a bioreactor, as plant propagule source, located upstream of the disperser unit;
   b. orientation and sorting unit for orienting and sorting the plant propagules suspended in a fluid, located downstream of the separator device; and
   c. a deposition device, located downstream of the orientation and sorting unit, if present.

25. The method according to claim 3, wherein the method is adapted for continuous operation such that it comprises feeding fluid into the separator container at a rate exceeding the rate of fluid flow from the conduit.

26. The system according to claim 24, the system comprising the deposition device, wherein the deposition device is for depositing fluid-suspended plant plant propagules while maintaining the orientation of the plant propagule and the deposition device comprises:
   i. a flow channel dimensioned such that the plant propagules may travel with fluid flowing through the channel but are restricted to travelling either in a crown-first or crown-last orientation by dimensional constraints, said flow channel emanating to an outlet;
   ii. an plant propagule receiver; and
   iii. means of forming a free jet of fluid emanating from the outlet, wherein the free jet during operation is aligned with an plant propagule receiver thus allowing plant propagules suspended in the fluid to be deposited in the plant propagule receiver; wherein the means of forming a free jet comprise a flow channel section immediately upstream of the outlet having a straight section with length at least equal to the largest cross-sectional inside dimension of the flow channel.

27. The system according to claim 26, wherein the length of the straight section of the deposition device is at least 10 times the largest cross-sectional inside dimension of the flow channel.

28. The system according to claim 26, wherein a tip of the outlet of the deposition device is configured to be positioned during operation at one to three flow channel diameters away from the plant propagule receiver.

* * * * *